United States Patent
Sintov et al.

(10) Patent No.: US 6,667,052 B2
(45) Date of Patent: *Dec. 23, 2003

(54) TRANSDERMAL DELIVERY SYSTEM

(75) Inventors: Amnon Sintov, Omer (IL); Uri Wormser, Even Shmuel Street 55/2, Jerusalem (IL), 97230

(73) Assignees: Ben Gurion University of the Negev Research and Development Authority, Beer Sheva (IL); Uri Wormser, Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 09/928,131

(22) Filed: Aug. 10, 2001

(65) Prior Publication Data

US 2002/0164366 A1 Nov. 7, 2002

Related U.S. Application Data

(63) Continuation-in-part of application No. 09/424,525, filed as application No. PCT/IL98/00205 on May 4, 1998, now Pat. No. 6,274,166.

(30) Foreign Application Priority Data

May 29, 1997 (IL) .................................................. 120943

(51) Int. Cl.[7] ......................... A61F 13/00; A61F 13/02; A61L 15/16
(52) U.S. Cl. ...................... 424/449; 424/448; 424/443; 514/946
(58) Field of Search .............................. 424/449, 448, 424/443; 514/946

(56) References Cited

U.S. PATENT DOCUMENTS

| | | | |
|---|---|---|---|
| 4,229,410 A | * | 10/1980 | Kosti ............................ 4/222 |
| 4,545,990 A | | 10/1985 | LeFoyer de Costil et al. |
| 5,047,249 A | | 9/1991 | Rothman et al. |
| 5,707,641 A | | 1/1998 | Gertner et al. |
| 6,274,166 B1 | * | 8/2001 | Sintov et al. ................ 424/443 |

FOREIGN PATENT DOCUMENTS

| | | | | |
|---|---|---|---|---|
| WO | WO 85/05036 A1 | * | 11/1985 | |
| WO | WO 90/00899 A1 | * | 2/1990 | .......... A61K/37/12 |
| WO | WO 90/01023 A1 | | 2/1990 | |
| WO | WO 96/11705 A1 | | 4/1996 | |

OTHER PUBLICATIONS

Morgan, et al., "Participation of Cellular Thio/Disulphide Group on the Uptake, Degradation and Bioactivity of Insulin in Primar Cultures of Rat Hepatocytes", Biomedical Journal, vol. 2, pp. 349–356.*

Morgan, M.S. et al. "Participation of Cellular Thiol/Disulphide Groups on the Uptake, Degradation and Bioactivity of Insulin in Primary Cultures of Rat Hepatocytes" *Biomedical Journal*, vol. 2, pp. 349–356.

* cited by examiner

*Primary Examiner*—Thurman K. Page
*Assistant Examiner*—Isis Ghali
(74) *Attorney, Agent, or Firm*—Leydig Voit & Mayer, Ltd.

(57) ABSTRACT

The invention provides a transdermal delivery system for treating diabetes and other pathologic systemic conditions, comprising an active ingredient selected from the group consisting of peptides and proteins having an S—S bond and mixtures thereof and a pharmaceutically acceptable oxidizing agent selected from the group consisting of iodine, povidine-iodine and sources thereof, said system being essentially free of reducing agents and said oxidizing agent enabling and facilitating the penetration of said active ingredient through the skin layers and into the blood stream.

8 Claims, 20 Drawing Sheets

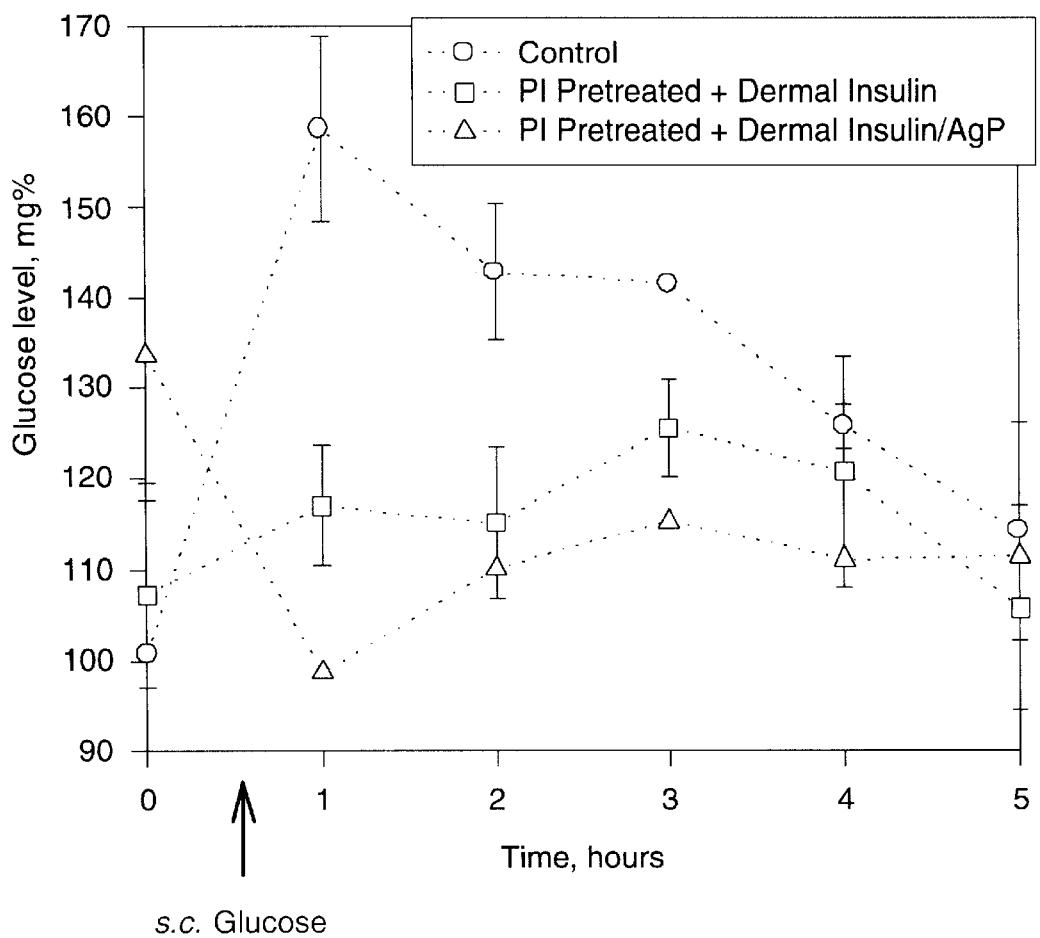

s.c. glucose

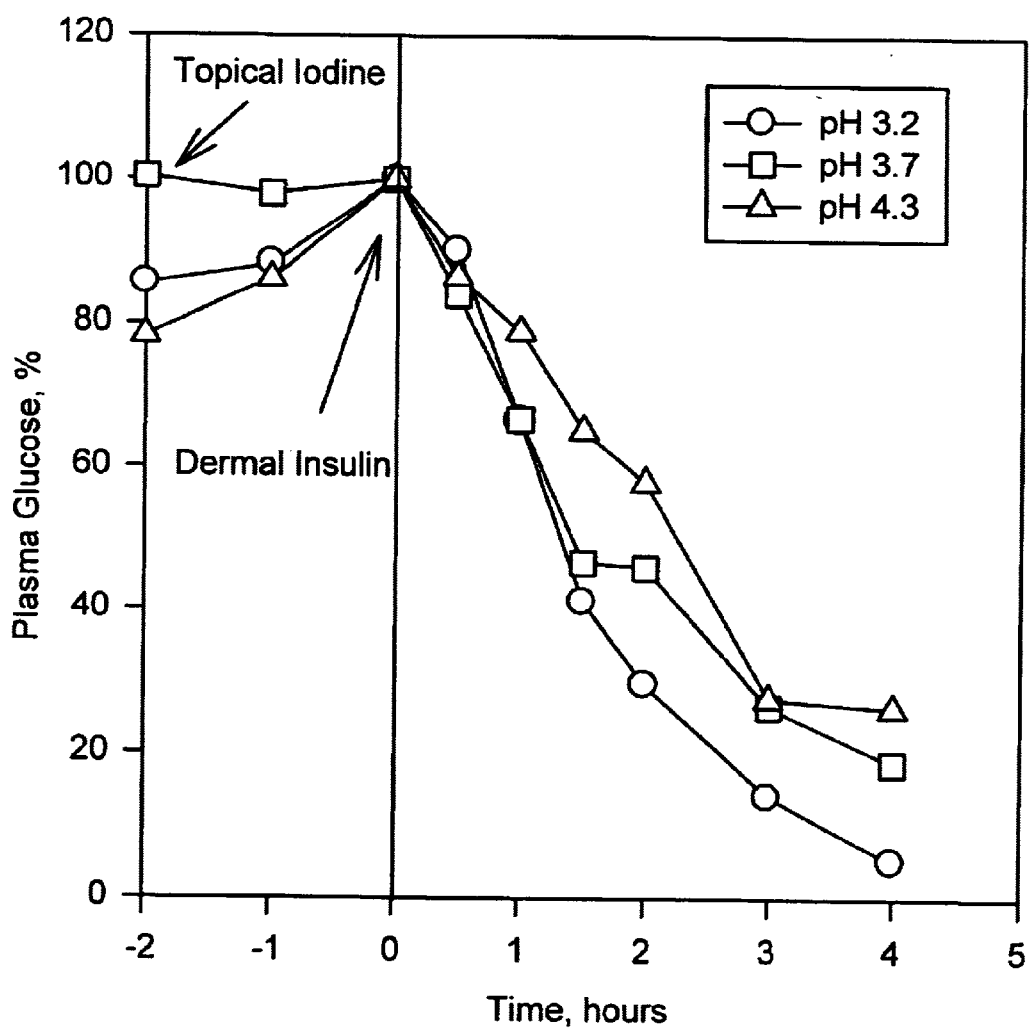

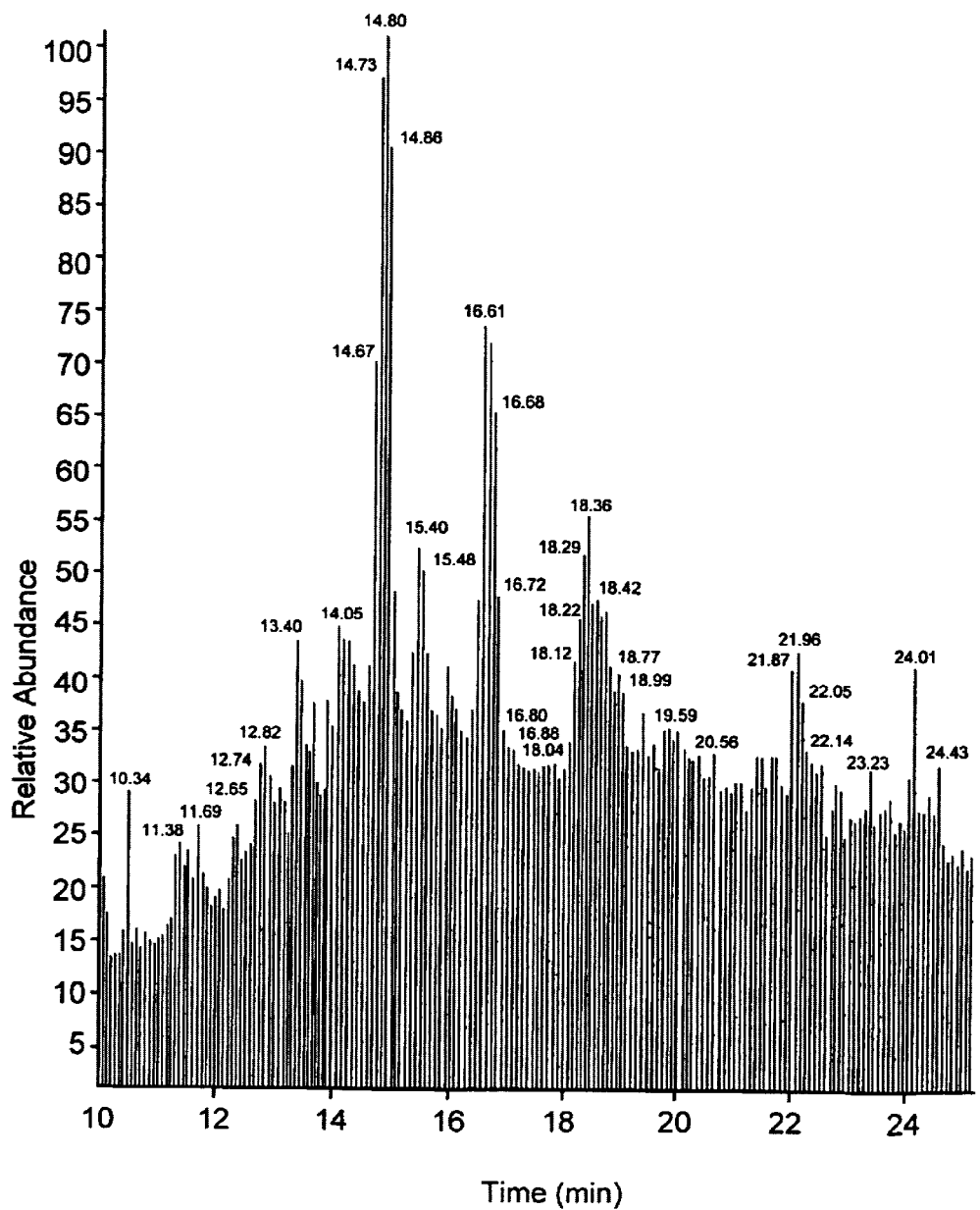

TRANSDERMAL DELIVERY SYSTEM

Figure 1:
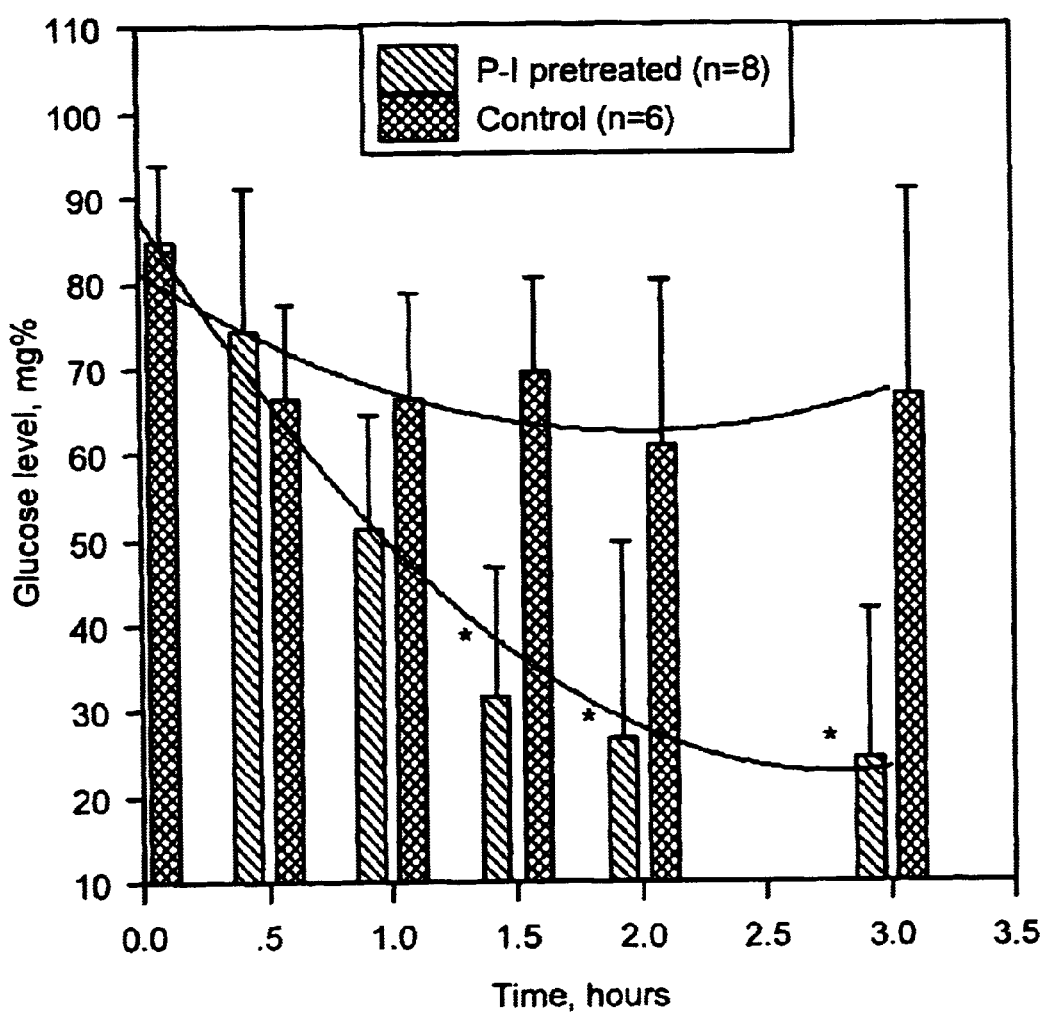
Figure 2A:
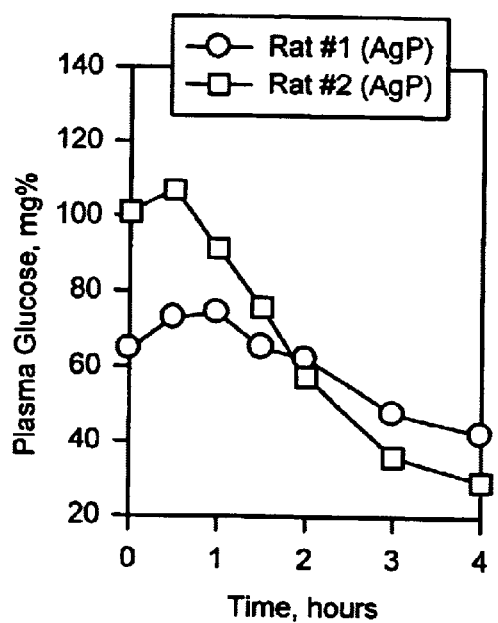
Figure 2B:
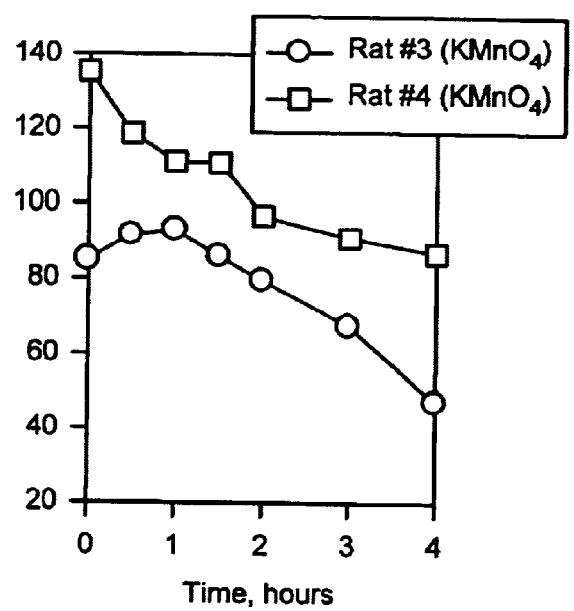
Figure 2C:
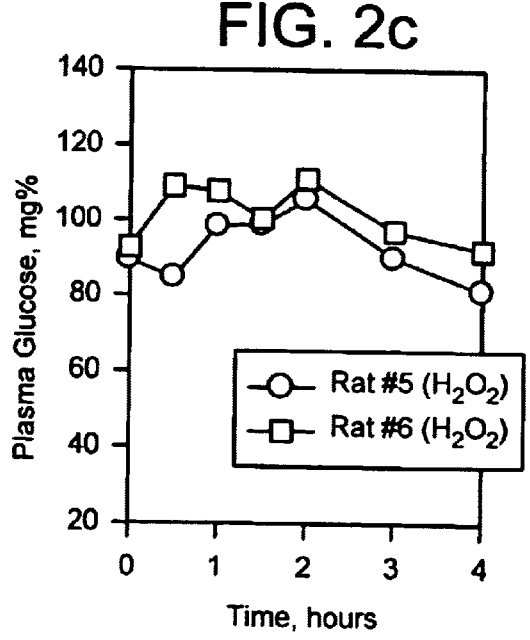
Figure 2D:
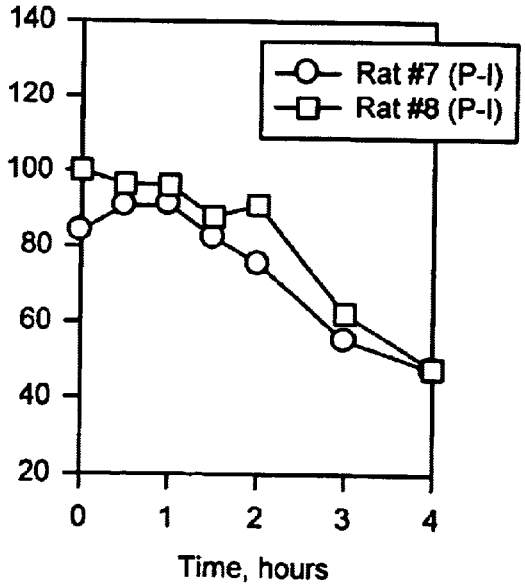

The present invention is a continuation-in-part of U.S. Application Ser. No. 09/424,525 filed Nov. 23, 1999, now U.S. Pat. No. 6,153,218, which is a 371 national stage of International Application No. PCT/IL98/00205 filed May 4, 1998 which in turn claims priority to IL 120943 filed May 29, 1997.

FILED OF THE INVENTION

The present invention relates to a transdermal delivery system containing an active ingredient selected from the group consisting of peptides and proteins having an S—S bond and mixture thereof. These systems incorporate further components that assist in stabilizing the active material, e.g., by preventing the inactivation thereof and facilitating the penetration thereof as active molecules through the skin layers.

It has been discovered in the present invention that oxidizing agents such as iodine, povidine-iodine, potassium permanganate, peroxides and silver protein enable the application of formulations containing proteins and peptides and especially insulin onto the skin.

Insulin is secreted from beta cells of pancreatic Langerhans islet in its active form. The human insulin is composed of two polypeptides, the A and B chain, usually of 21 and 30 amino acids residues, respectively, with a molecular mass of about 5800 Dalton. The peptides are interconnected by disulfide bonds of the cysteine residues at A7-B7, A20-B19 and A6-A11. Insulin exerts a wide variety of biological activities including controlling the uptake, utilization, and storage of cellular nutrients such as glucose, amino acids and fatty acids. The important target tissues of insulin are liver, muscle and fat but many other cell types are also influenced by this hormone. [Davis, S N; Granner,D K (1996) In: Goodman & Gilman's The Pharmacological Basis of Therapeutics. ninth edition ed. (Eds: Hardman,J G et al.) McGraw-Hill, 1487–15171].

One of the main physiological roles of insulin is stimulation of glucose transport into muscle and adipose tissues. A defect in this system leads to the diabetes mellitus syndrome characterized by hyperglycemia, changes in the metabolism of carbohydrates, lipids and proteins, and by elevated incidence of vascular disorders. There are two main diabetes, insulin-dependent diabetes mellitus (IDDM) with an incidence of 1–43 per 100,000 inhabitants in the Western countries, and the non-insulin-dependent diabetes mellitus (NIDDM) whose incidence is between 100–800 per 100,000 inhabitants in the Western countries (The above reference).

Insulin is the main treatment of all IDDM and many NIDDM patients. Long-term treatment is predominantly based on subcutaneous administration of insulin formulations. There are long-, short- and intermediate-acting preparation which are used according to the special requirements of the patient. However, apart from the discomfort and troublesome feelings and the possibility of infection associated with daily injections along the entire lifetime (particularly with IDDM, formerly termed juvenile-onset diabetes mellitus), this kind of therapy has serious clinical problems mainly with the maintenance of the appropriate blood levels of the hormone resulting in non-physiological blood glucose levels and other complications. Although much effort has been made in developing insulin analogs [Brange,J; et al. (1990) Diabetes 13, 923–954] and genetic engineering methodologies [Sutherland, DER et al. (1989) Diabetes 38 Suppl 1, 46–54], there are no successful findings for solving the clinical problems associated with parenteral insulin injections.

One of the approaches aimed to cope with this difficulty was to deliver the hormone non-invasively, via transdermal route of administration. By this procedure, the annoyance and inconvenience of the parenteral injections can be avoided; moreover, much steadier blood hormone levels can be achieved due to prolonged delivery of the drug. Several low molecular weight drugs have been formulated and are being clinically used as transdermal preparations. However, apart from a few medicines, many drugs, particularly peptides and proteins, are not successfully formulated for transdermal delivery. In vitro experiments have shown that α-melanocyte stimulating hormone analog can penetrate across human and mouse, but not in rat skin [Dawson, B V et al. (1990) J. Invest. Dermatol. 94, 432–435; Dawson, B V et al. (1988) Life. Sci. 43, 1111–1117] and that enkephalin can penetrate hairless mouse skin but in the presence of the enhancer n-decylmethyl sulfoxide and proteinase inhibitors [Choi,H K et al. (1990) Pharm. Res. 7, 1099–1106]. However, apart from one study with small number of mice which showed reduced levels of blood glucose after 4 hours of cutaneous application of insulin with enhancer [Liedtke,R K et al. (1990) Drug Res. 40, 880–883], no efficient in vivo transdermal penetration of peptides and proteins, by chemical means (e.g. enhancer or proteinase inhibitors) have been published.

Transdermal penetration of various peptides and proteins can be enhanced by iontophoresis using electrical current for delivering charged agents across the skin. Various peptides and small proteins including insulin, calcitonin, vasopressin, luteinizing hormone-releasing hormone, leuprolide, thyrotropin-releasing hormone and cholecystokinin were tested in in vitro iontophoresis assays and some of them also in in vivo systems [Heit,M C et al. (1993) J Pharm Sci 1993 82(3):240–243; Srinivasan,V et al. (1990) J. Pharm. Sci. 79, 588–591; Burnette,R R and Marrero,D (1986) J. Pharm. Sci. 75, 738–743; Banga,A K and Chien,Y W (1993): Pharm. Res. 10, 697–702; Mao,X M et al. (1995) Yao. Hsueh. Hsueh. Pao. 30, 302–306; Mao,X M et al. (1995) Yao. Hsueh. Hsueh. Pao. 30, 881–885; Meyer,B R et al. (1989) Am. J. Med. Sci. 297, 321–325]. Additional technique to facilitate transdermal delivery of insulin by ultrasound vibration, termed sonophoresis, was used in both in vitro and in vivo systems [Tachibana,K and Tachibana,S (1991): J. Pharm. Pharmacol. 43, 270–271; Tachibana,K (1992) Pharm. Res. 9, 952–954; Mitragotri,S et al. (1995) Science. 269(5225), 850–853]. Although transdermal penetration of insulin and other proteins and peptides was enhanced by the sonophoretic and iontophoretic techniques, these procedures require complicated and an uneasy way of operation. Furthermore, the safety of long-term, daily use of this technique was not confirmed. The fact that only one report, describing unsatisfactory results on the use of penetration enhancer in type II diabetic patients [Liedtke,R K et al. (1990): Drug Res. 40, 884–886] have been published, indicates the problematic issues of the above methods.

According to U.S. Ser. No. 09/424525 there is provided a transdermal delivery system for treating diabetes and insulin influenced pathologic systemic conditions comprising insulin and a pharmaceutically accepted oxidizing agent selected from the group consisting of permanganate and silver protein, said oxidating agent enabling and facilitating the penetration of said insulin through the skin layers and into the blood stream.

According to the present invention there is now provided a transdermal delivery system for treating diabetes and other pathologic systemic conditions, comprising an active ingredient selected from the group consisting of peptides and proteins having an S—S bond and mixtures thereof and a pharmaceutically acceptable oxidizing agent selected from the group consisting of iodine, povidine-iodine and sources thereof, said system being essentially free of reducing agents and said oxidizing agent enabling and facilitating the penetration of said active ingredient through the skin layers and into the blood stream.

As will be discussed hereinafter it is believed that said oxidizing agent serves to oxidize reduced glutathione thereby preventing its functioning as an inactivating agent.

Assuming that this hypothesis is correct then also a component such as buthionine sulfoximine, which also prevents the formation of glutathione can be used in the present invention alone or in combination with an oxidizing agent to achieve the desired effect.

In preferred embodiments of the present invention said active ingredient is insulin.

In WO 90/00899 by Rothman there are described compositions for treating conditions of keratinous tissue in mammals including wounds, sebborhea, psoriasis, dandruff, acne, itching, allergic reactions, non-specific dermatitis eczematoid dermatitism chronic dermatitis, equine exuberant granuloma, decubitis ulcers, and canine cutaneous granulomas which compositions include an activated protein component a compatible reducing agent and an oxidizing agent. While said compositions include a protein and an oxidizing agent and are applied to the skin the types of treatments disclosed therein are completely different from the transdermal delivery system of the present invention and as demonstrated in the comparative hereinafter the compositions of said publication are incapable of achieving a transdermal effect. In the present invention oxidizing agents are used to facilitate transdermal delivery of proteins and peptides having an S—S bond across a healthy and intact skin into the blood stream to achieve a systemic effect such as, for example, in the case of insulin, the reduction of blood glucose levels. The use of transdermal delivery systems to treat systemic diseases differs form the local treatment of skin illnesses described in Rothman. The disclosure in Rothman does not relate to the delivery of proteins through skin into the blood stream. Instead, the compositions of Rothman contain proteins and oxidizers that are used to facilitate skin healing. In the present invention, however, the oxidizer prevents the reduction of disulfide bonds in the active ingredient and, thus, the structure of the active protein or peptide is retained therby enabling the systemic activity of the inventive transdermal delivery system.

Moreover, the compositions disclosed in Rothman contain a reducing agent as an essential ingredient thereof and an optional oxidizing agent. Although a therapeutic composition containing both a reducing agent and an oxidizing atent may successfully treat diseased skin according to Rothman, such a composition does not and cannot provide the desired transdermal delivery of a protein and/or peptide containing an S—S bond into the blood stream, since the presence of the reducing agent required by Rothman counteracts the function of the oxidizing agent in facilitating the penetration of the active ingredient through the skin.

Thus, in preferred embodiments of the present invention there is also provided a transdermal delivery system for treating diabetes and other pathologic systemic conditions, comprising an active ingredient selected from the group consisting of peptides and proteins having an S—S bond and mixtures thereof and a pharmaceutically acceptable oxidizing agent selected from the group consisting of iodine, povidine-iodine, potassium, permanganate, peroxides and silver protein and sources thereof, said system being essentially free of reducing agents and said oxidizing agent enabling and facilitating the penetration of said active ingredient through the skin layers and into the blood stream.

In initial in vivo studies, employing insulin-containing wells on rat abdominal skin, no reduction in blood glucose levels was observed. Nevertheless, insulin quantities were significantly decreased in the open wells. This discrepancy may be associated with the ability of reduced glutathione (GSH) (and of other cellular SH groups) to inactivate insulin by reducing its disulfide bond(s) [Rafter,G W (1990) Biochem. Int. 20, 817–820] followed by aggregation of several peptide molecules in the in vivo system. The opposite situation can also occur by the virtue of this invention, i.e. the effect of high levels of GSH (and other SH groups), could be overcome by topical pretreatment of the skin with oxidizing agents (such as povidone iodine, iodine alone and/or silver protein), resulting in oxidation of the cellular GSH (and other R-SH groups) to form the inactive GSSG (and/or R-SS-R). Reduced levels of the former as well as other SH containing agents prevent inactivation of insulin, enabling hormone penetration via skin into the blood stream and reduction in blood glucose levels. All tested oxidants resulted in time-dependent reduction in blood glucose levels, whereas rats without such pretreatment or treatment failed to show this phenomenon.

Povidone iodine (PI) (polyvinylpyrrolidone-iodine complex) ointment is widely used as an antiseptic agent. The successful combination of being safe and non-irritant as well as an efficient antiseptic agent was already demonstrated 40 years ago [Shelanski,H A and Shelanski,M V (1956) J. Int. Coll. Surg. 25, 727–734]. The fact that PI is commonly employed in hospitals, clinics and home use is further corroboration for its advantageous properties. Other oxidants such as silver protein (mild or strong) and permangnates, have been used for many years may also be employed in the compositions of this invention.

In the practice of this invention topical proteins such as insulin in therapeutically effective doses are incorporated into pharmaceutically acceptable carriers such as gels, ointments, solutions, paste, powder, and adhesive patch. The resulting formulations are applied to the skin of patients as many applications as needed, preferably once a day. The novel carriers contain insulin or other protein drugs that are not stable in vital skin in-vivo, thus need a protecting agent against skin biotransformation before approaching the systemic blood. The present invention comes to challenge the prior art, which considers the skin as a physical barrier to proteins such as insulin. It has been clearly proved that 5807-dalton human insulin quantitatively penetrates an excised skin in-vitro and in-vivo, but is inactivated through the in-vivo transport. This inactivation can be diminished by using oxidants such as povidone-iodine or silver protein. It has been hypothesized that these mild oxidizing agents result to a reduction in skin levels of glutathione and other reducing agents, thus preventing insulin inactivation caused by dimerization, aggregation, cleavage to two separate chains, cleavage of one S—S bond, etc.

The invention is derived, in part, from the discovery that the delivery of topically-applied protein drugs having an S—S bond into the blood circulation is possible only if oxidizing agents are involved before or during the application.

The present invention relates to transdermal delivery of peptide/protein drugs having an S—S bond. The preferred compositions comprise a safe and effective quantities of: (a) a therapeutic protein/peptide, (b) an oxidant such as iodine or povidine-iodine, or another source of iodine or combinations of oxidants, (c) an appropriate vehicle system which may contain skin penetration enhancers selected from those known in the art (see, e.g., Ghosh, T. K., Pfister, W. R., and Yum, S. I., Transdermal and Topical Drug Delivery Systems, 1997, Interpharm Press, Inc., pp.357–509).

Effective levels of protein drugs are delivered by the novel compositions. An "effective" level is meant that a concentration of a drug is high enough to be effective in treating the condition in which the drug has been designed to treat. Examples of protein drugs are: insulin, alpha-, beta-, and gamma-interferon, human growth hormone, alpha- and beta-1-transforming growth factor, granulocyte colony stimulating factor (G-CSF), granulocyte macrophage colony stimulating factor (G-MCSF), parathyroid hormone (PTH), human or salmon calcitonin, glucagon, somatostatin, vasoactive intestinal peptide (VIP), and LHRH analogs.

As mentioned above, povidone-iodine, iodine and sources thereof as well as silver protein are preferably selected as safe and effective "skin-protein-stabilizer" in a pretreatment procedure or in treatment composition at concentrations of 0.01% to 80%.

The therapeutic proteins and its protectors/stabilizers in-vivo, can be applied as a topical formulation such as cream (o/w or w/o), ointment, film-forming liquid spray, or gel using occlusive or non-occlusive dressings. A composition in an appropriate polymeric patch is preferable as transdermal protein delivery, and it consists of compatible adhesive polymers known in the art. The polymer can be selected from the group of acrylic polymers, cellulosic polymers, polyurethanes, polylactic/polyglycolic acids, polyamino acids, polysaccharides, polyurea, polyvinyl alcohol, polyvinylpyrrolidone (povidone), and natural proteins.

A transdermal patch can consist several layers: in the inner side a peelable plastic cover will protect the drug layer containing the adhesive polymer, plasticizer, the oxidizing agents, penetration enhancers and other excipients. The outer layers (i.e., the external layers) are designated to protect the drug from diffusion outward and to stick the patch by its margins to the skin, so the drug layer is occluded from all sides except the skin side where it is in close contact (see, e.g., Chien, Y. W., Transdermal Controlled Systemic Medications, 1987, Marcel & Decker, pp. 93–120, 365–378).

While the invention will now be described in connection with certain preferred embodiments in the following examples and with reference to the accompanying figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples, which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of the formulations procedures as well as of the principles and conceptual aspects of the invention.

EXAMPLE 1

A pharmaceutical formulation for transdermal purpose, containing silver protein:

| Composition | |
|---|---|
| insulin | 50 IU |
| Silver protein | 0.025 g |
| Water | 0.5 ml |

EXAMPLE 2

A pharmaceutical formulation for transdermal purpose, containing a penetration enhancer, administered after skin has been pretreated with povidone-iodine:

| Povidone - Iodine USP ointment | 0.5 g |
|---|---|
| Composition of insulin formula | |
| Insulin | 50 IU |
| Oleic acid | 15 mg |
| Propylene glycol | 150 mg |
| Water | 1 ml |
| adjust pH to: | 7.5–7.9 |

EXAMPLE 3

A pharmaceutical formulation for transdermal purpose, containing silver protein and a penetration enhancer, administered after skin has been pretreated with povidone-iodine:

| Povidone - Iodine USP ointment | 0.5 g |
|---|---|
| Composition of insulin formula | |
| Insulin | 50 IU |
| Silver protein | 25 mg |
| Oleic acid | 15 mg |
| Propylene glycol | 150 mg |
| Water | 1 ml |
| adjust pH to: | 7.5–7.9 |

EXAMPLE 4

Pharmaceutical formulations for transdermal purpose, containing insulin (composition A) or insulin with silver protein and penetration enhancers (composition B), administered after skin has been pretreated with molecular iodine in tetraglycol:

| 5% iodine solution | |
|---|---|
| Iodine | 0.5 g |
| Tetraglycol | 9.5 g |
| Or: | |
| 2% iodine solution in water/tetraglycol* | |
| Iodine | 0.2 g |
| Tetraglycol | 5.0 g |
| Distilled water | 4.8 g |
| Or: | |
| 2% iodine ointment (or gel) in water/tetraglycol* | |
| Iodine | 0.2 g |
| Tetraglycol | 5.0 g |
| Polyvinyl pyrrolidone (Povidone K-90) | 1.0 g |
| Distilled water | 3.8 g |

-continued

| Composition of insulin formula A | |
|---|---|
| Insulin injectable solution (e.g., Humulin R) | 50 IU |
| PH adjusted to: | 6.0–7.0 |
| Composition of insulin formula B | |
| Insulin | 50 IU |
| Silver protein | 25 mg |
| Oleic acid | 15 mg |
| Propylene glycol | 150 mg |
| Water | 1 ml |
| adjust pH to: | 7.5–7.9 |

*pH can be adjusted with $Na_2HPO_4 X\ 12H_2O$

Comparative Example 5

In-vivo evaluation of dermally-applied insulin and povidone-iodine Animals: Locally-grown rats (Sprague-Dawley strain) were anesthetized after overnight fast (15 mg/ml pentobarbital sodium, 0.2–0.3 ml i.p.). The rats were placed on their back, the abdominal hair was trimmed off, and then the skin was washed gently with distilled water. The animals were maintained with 0.1 ml pentobarbital 15 mg/ml solution to keep them continuously asleep during the experiment.

Insulin application: Small cylinders (13 mm diameter orifice) were attached on the central part of the rat abdomen by silicon glue. Doses of 0.5 ml of Humulin R solution for injection (equivalent to 50 IU human insulin) were pippeted into the open cylinders. In some experiments insulin solution contained other ingredients such as penetration enhancers (i.e., sodium oleate, propylene glycol) or an oxidant (i.e., mild silver protein BPC—Argirol, Givaudan, France). Careful attention was paid that the liquid has covered the entire skin area in the cylinder and that no leaking has occurred.

Pretreatment: Before insulin application (in cases where a combined treatment was not studied), the skin was treated with antioxidants by spreading of povidone-iodine ointment (PI, Polydine—Fischer, Israel) for 0.5–3 hours, or was exposed to an oxidant in aqueous solution using the above cylinder attachment procedure.

Blood sampling and plasma glucose monitoring: Blood samples (ca. 200 ml) were taken from the tail vein into 0.5-ml tubes containing 5 ml heparin solution (5000 i.u./ml, Laboratoire Choay, France). The tubes were centrifuged (5000 rpm, 5 minutes), and 10 ml of separated plasma was transferred with 1 ml of GOD/PAP reagent solution (Glucose PAP kit, Hoffman-La Roche, basel, Switzerland). The absorbance of developed color was read measured at 500 nm wavelength, against blank and an appropriate calibration curve.

Results: FIG. 1 demonstrates the first evidence for the essence of this invention. It has been definitely shown that in an in-vivo experiment, a pretreatment with an oxidizing agent, Povidone-Iodine (PI) ointment, and insulin application on the skin produces a significant reduction in plasma glucose levels. For comparison, plasma levels in control animals, which were not treated with PI, were not influenced by dermal insulin. As already described in the background section, it has been surprisingly found according to this invention that the skin is not a physical barrier for insulin and other polypeptides. It seems that protein metabolism or biotransformation occurs in the skin during transport of the molecules. It has been proved that this biotransformation occurs only in live animals and not in excised skin tissues, no matter how fresh they are.

Comparative Example 6

In-vivo evaluation of dermally-applied insulin and various oxidants

Eight (8) locally-grown rats (Sprague-Dawley strain) were anesthetized after overnight fast (15 mg/ml pentobarbital sodium, 0.2–0.3 ml i.p.). The rats were placed on their back, the abdominal hair was trimmed off, and then the skin was washed gently with distilled water. The animals were maintained with 0.1 ml pentobarbital 15 mg/ml solution to keep them continuously asleep during the experiment. In 6 of the rats, small cylinders (13 mm diameter orifice) were attached on the central part of the rat abdomen by silicon glue. The cylinders were filled with aqueous aliquots (0.5 ml) of oxidizing agents—2 cylinders with 5% silver protein solution, 2 cylinders with 0.01% potassium permangnate, and 2 cylinders with 9% hydrogen peroxide. The two remaining animals were pretreated with povidone-iodine as already described in example 5. After 3 hours, the cylinders were emptied or the iodine was washed out of the skin, then doses of 0.5 ml of Humulin R solution for injection (equivalent to 50 IU human insulin) were pippeted into the open cylinders.

Blood sampling and glucose measurement were performed as described in example 5.

Results: FIG. 2 presents the effectiveness of the four oxidants in facilitating plasma glucose reduction by dermally-applied insulin. It can be seen that glucose levels reduced significantly in silver protein, $KMnO_4$, and povidone-iodine pretreated rats. No glucose reduction occurred in rats pretreated with 9% hydrogen peroxide solution, probably because peroxides are sensitive to peroxidase and catalase enzymatic reactions. If peroxides are selected, less sensitive and long lasting compounds should be used (i.e., carbamide peroxide) for this purpose.

Comparative Example 7

In-vivo evaluation of dermally-applied insulin after diethyl maleate (DEM) pretreatment Two non-fasted locally-grown rats (Sprague-Dawley strain) were anesthetized (15 mg/ml pentobarbital sodium, 0.2–0.3 ml i.p.). The rats were placed on their back, the abdominal hair was trimmed off, and then the skin was washed gently with distilled water. The animals were maintained with 0.1 ml pentobarbital 15 mg/ml solution to keep them continuously asleep during the experiment. Diethyl maleate, a glutathion depleting agent, was injected intraperitoneally (0.5 ml, 20% v/v ethanolic solution) to one rat only. Small cylinders (13 mm diameter orifice) were attached on the central part of the rat abdomen by silicon glue. The cylinders were filled with aqueous aliquots (0.5 ml) of Humulin R solution for injection (equivalent to 50 IU human insulin).

Blood sampling and glucose measurement were performed as described in example 5.

Figure 3:
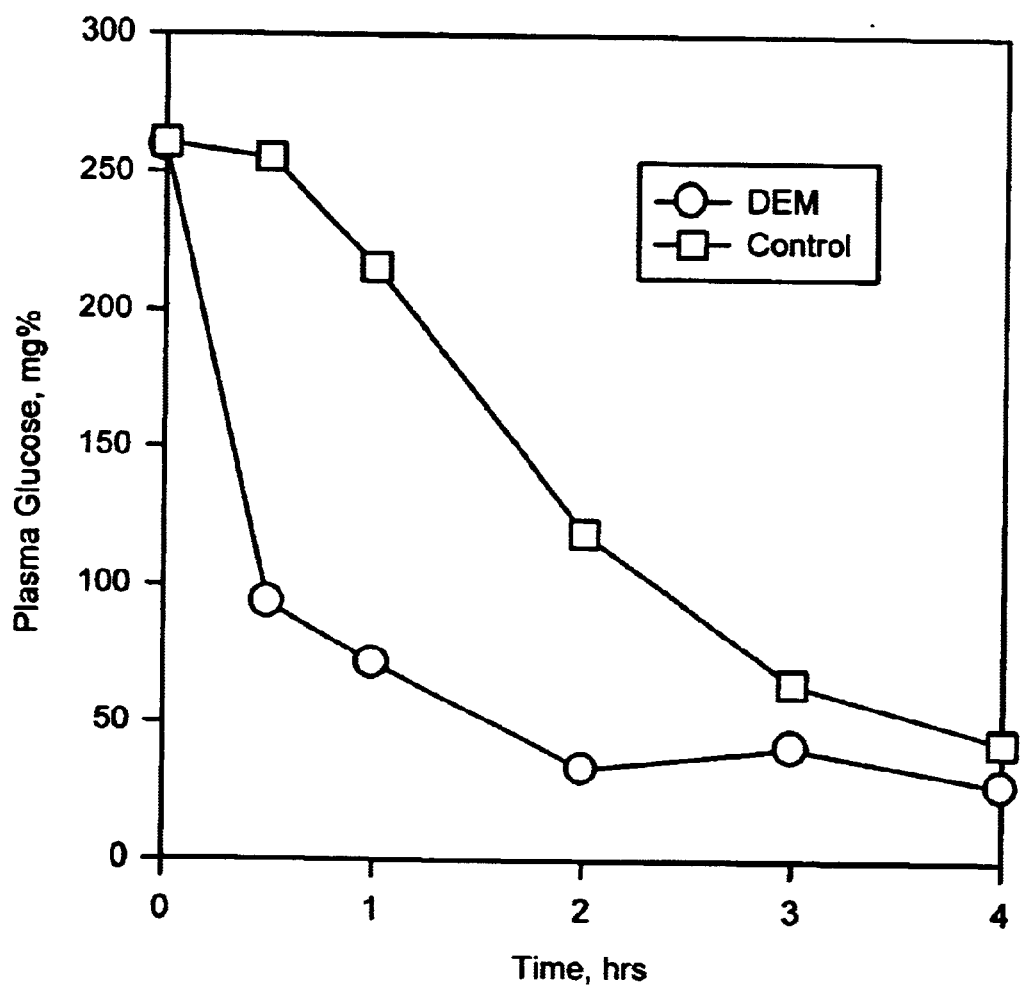

Results: FIG. 3 shows the abrupt reduction of plasma glucose in the DEM-treated rat formed by the skin transport of active insulin. In comparison, the plasma glucose in the untreated rat decreased relatively slower, a reduction that was driven by endogenous insulin in the fasted state.

Comparative Example 8

In-vivo evaluation of dermally-applied insulin co-administered with silver protein, following pretreatment with povidone-iodine Six (6) locally-grown rats (Sprague-Dawley strain) were anesthetized after overnight fast (15 mg/ml pentobarbital sodium, 0.2–0.3 ml i.p.). The rats were placed on their back, the abdominal hair was trimmed off, and then the skin was washed gently with distilled water. The animals were maintained with 0.1 ml pentobarbital 15 mg/ml solution to keep them continuously asleep during the experiment. Three of the animals were used as untreated control group, while the rest were pretreated with povidone-iodine ointment as described in example 5, except that only 30-min application was performed instead of 3 hours. After the ointment was gently washed out, small cylinders (13 mm diameter orifice) were attached on the central part of the rat abdomen by silicon glue. The cylinders were filled with 0.5 ml of Humulin R solution for injection (equivalent to 50 IU human insulin) in the control group, and 0.5 ml Humulin R solution containing 5% silver protein in the treatment group.

Blood sampling and glucose measurement were performed as described in example 5.

Figure 4A:
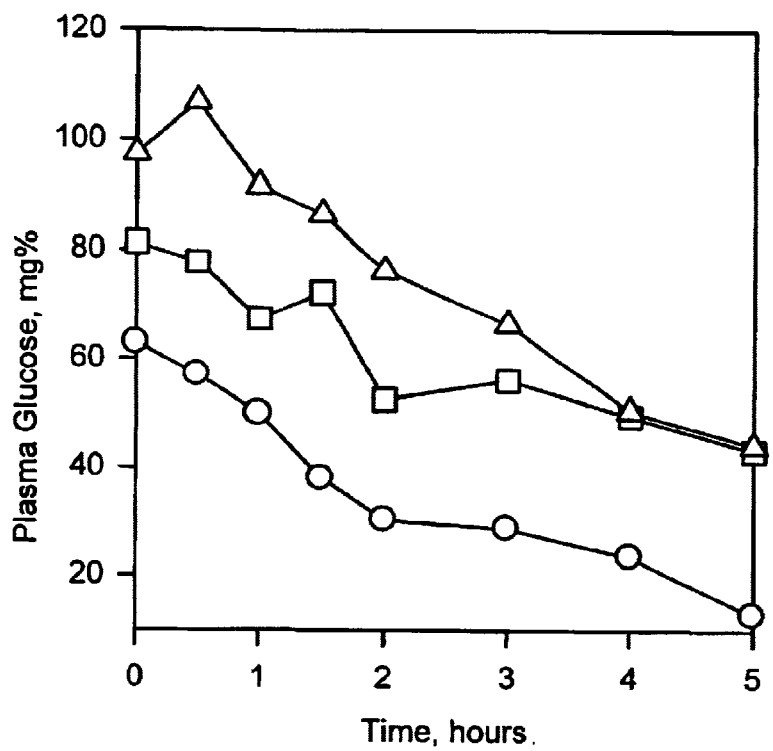
Figure 4B:
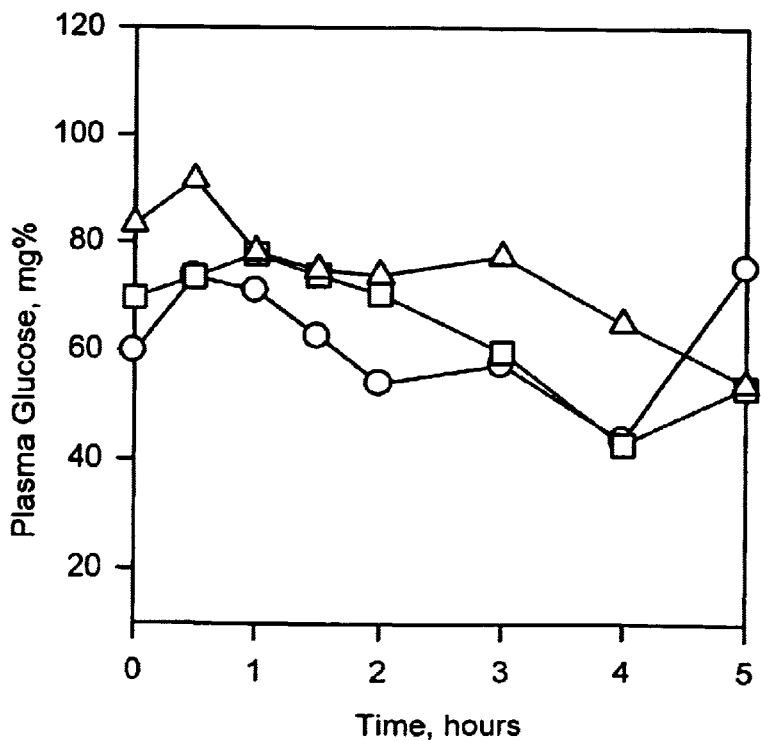

Results: FIG. 4 presents the effectiveness of the treatment in facilitating plasma glucose reduction by the dermally-applied insulin. As it is shown in the Figure, a consistent reduction rate in glucose levels was monitored in the treated rats, while the untreated rats demonstrated almost the same levels with no change.

Comparative Example 9

In-vivo evaluation of dermally-applied insulin and povidone-iodine

This experiment used the same protocol as in example 5 and this is actually a repetition of the study aimed to examine the contribution of povidone-iodine in delivering unchanged and active insulin transdermally.

Figure 5A:
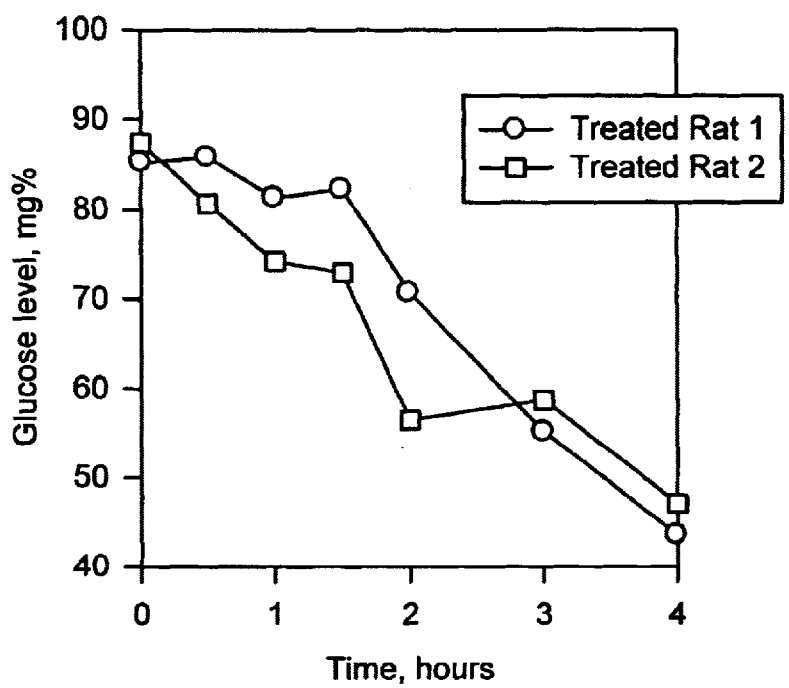
Figure 5B:
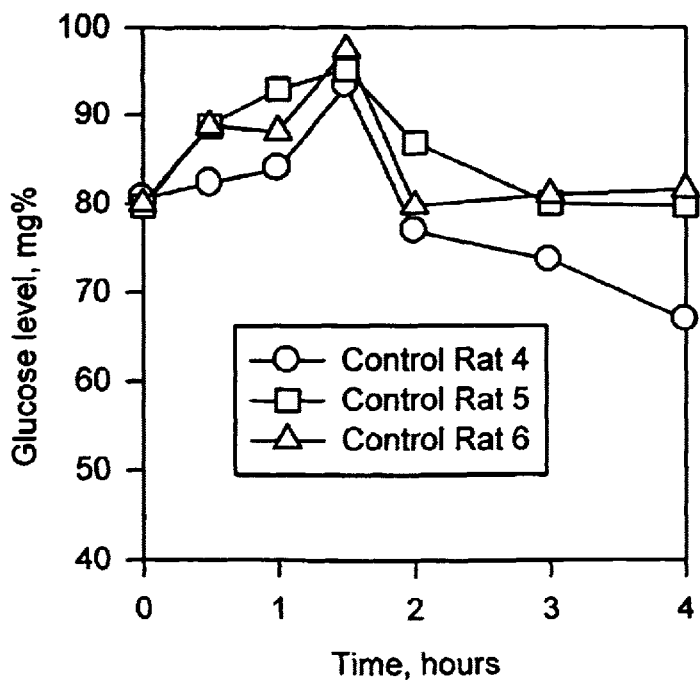

Results: FIG. 5 presents the effectiveness of the P-I pretreatment in facilitating plasma glucose reduction by dermally-applied insulin. While no change occurred in the control rats, plasma glucose decreased significantly in the P-I treated animals.

Comparative Example 10

Figure 6:
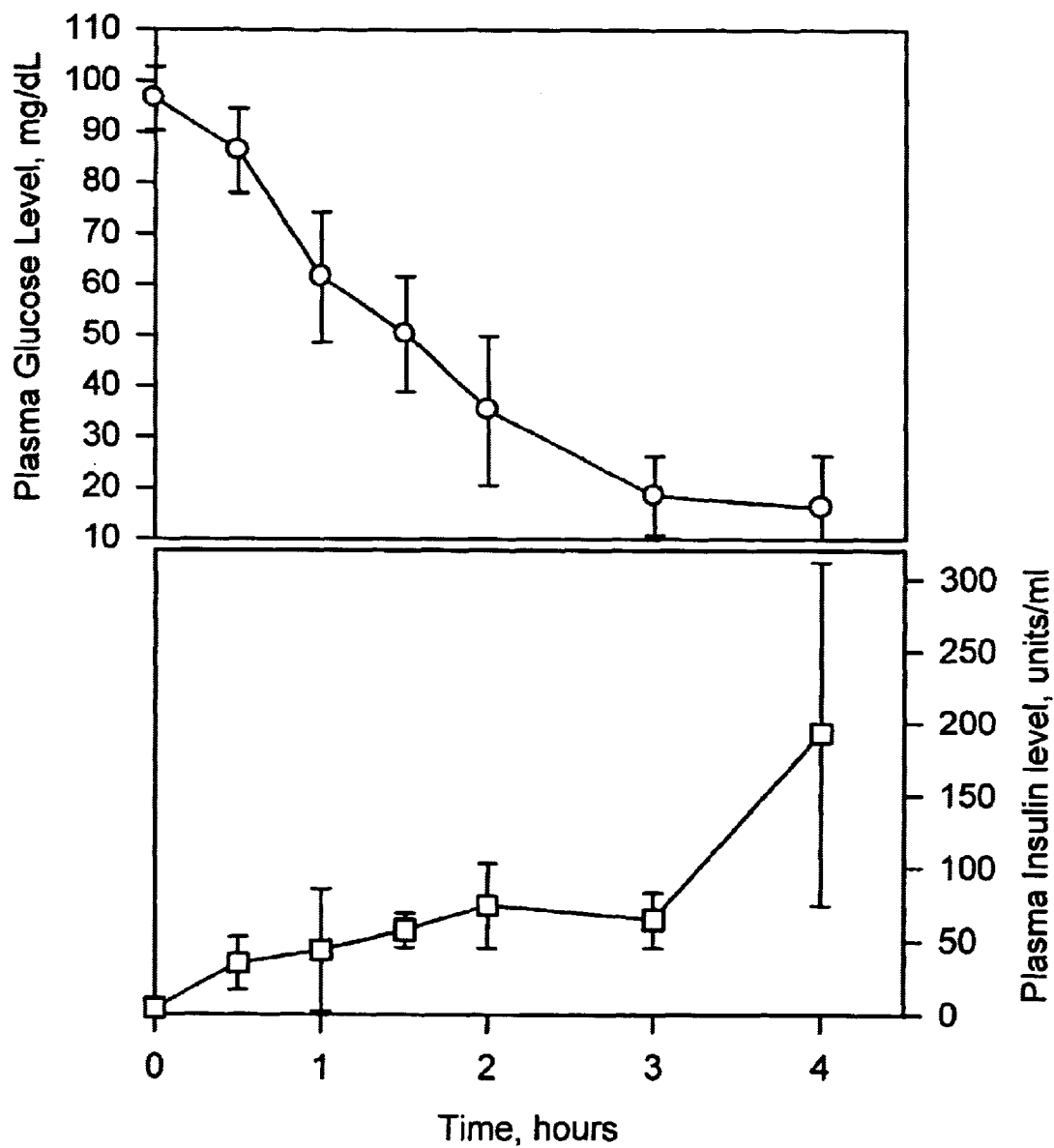

Anesthetized rats were pretreated with 2% iodine preparation for 3 hours, and then insulin was applied on the iodine-exposed skin (as described in Example 5). As can been seen in FIG. 6, a significant hypoglycemic response was observed with a concomitant elevation of circulating insulin levels in plasma as measured by radioimmunoassay. No elevation of plasma insulin levels was observed in control rats, which were not pretreated with iodine.

Figure 7B:
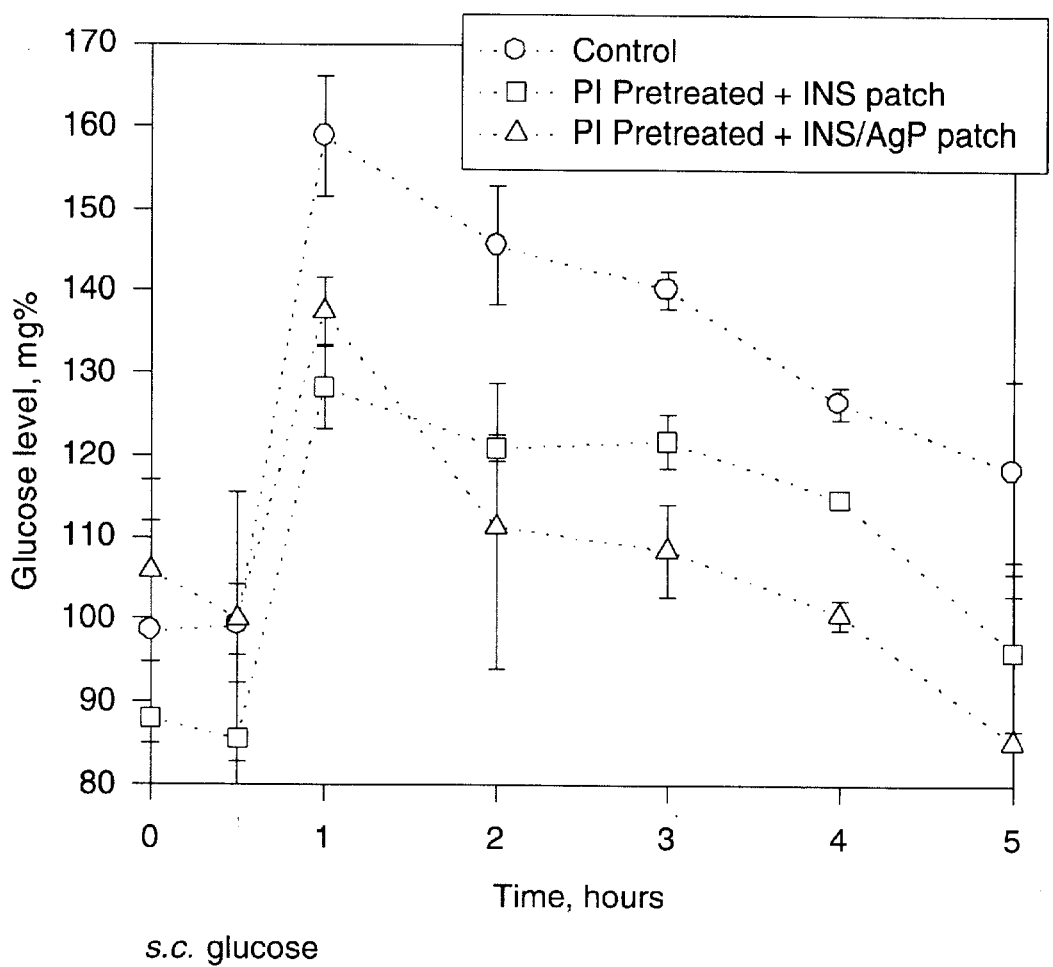

Interestingly, in both control and iodine-treated groups about 77% of the applied insulin remained in the cylinder after 3 hours, with no difference between groups (76.0±6.6% vs. 77.3±7.8%), however, since no pharmacological response was observed in the control group, the penetrating amount (~23% during 3 hours) underwent inactivation. After pretreatment with the oxidant this inactivation was inhibited and the penetrating insulin remained presumably in its active form. Similar results were obtained in previous studies with other mild oxidant such as silver protein and potassium permanganate. Further evidence was achieved in glucose tolerance tests done with and without PI pretreatment. FIGS. 7a and 7b present the results of these tests after the application of insulin solutions (a) and simple polymeric patches containing 50 units insulin (b).

Comparative Example 11

Anesthetized rats were pretreated for 3 hours with three different 2% iodine preparations with pH values of 3.2, 3.7 and 4.3, and then insulin was applied on the iodine-exposed skin (as described in Example 5). FIG. 8 showed a sharp decrease in glucose levels with very slight differences, which might depends on pH.

Comparative Example 12

The mechanism of insulin skin inactivation

Figure 9A:
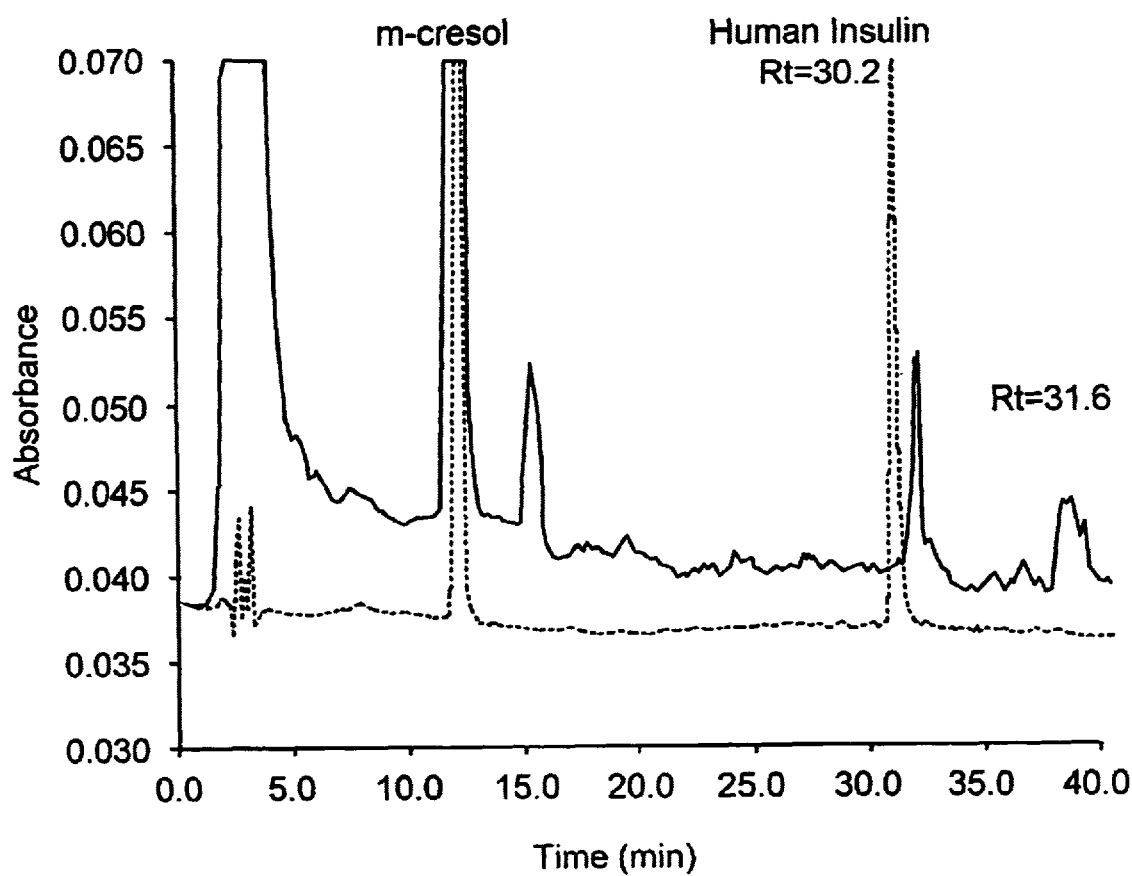

The fact that insulin penetrated into the skin but did not cause a reduction in plasma glucose levels, led us thinking that there are inactivation mechanisms in the skin. Our rationale was based on the assumption that the activity of various sulfhydryl compounds such as glutathione, thioredoxin or protein disulfide isomerase (PDI) may inactivate insulin by reduction of its disulfide bonds, consequently, the hormone may be inactivated during penetration by excess of sulfhydryl compounds present in the skin. An indication for this process may be obtained from the HPLC chromatogram of an ethanolic extract of 2-hr insulin-exposed skin (FIG. 9A). By using an assay published previously (Wroblewski V J, Masnyk M, Khambatta S S, Becker G W, Mechanism involved in degradation of human insulin by cytosolic fractions of human, monkey, and rat liver (1992): *Diabetes* 41, 539–547), we found that a new form of insulin was generated in the skin. Note in FIG. 9A that the peak with a retention time of 31.65 minutes obtained from the skin extract is different from the standard insulin (Rt=30.2), however, its molecular weight as determined by mass spectral analysis was 5807 dalton (similar to human insulin). After reacting the collected peak with N-ethylmaleiimide at pH=7.5 the peak disappeared, indicating that at least one of the disulfide bonds may be in a reduced form.

HPLC analysis: Gradient elution method was performed to isolate insulin forms extracted from insulin-exposed skin, with and without iodine pretreatment. The method was performed according to Wroblewski et al (see above) using a reverse phase column (Vydac $C_{18}$, 250×4.6 mm, 5? m), and a diodearray detector.

Figure 9B:
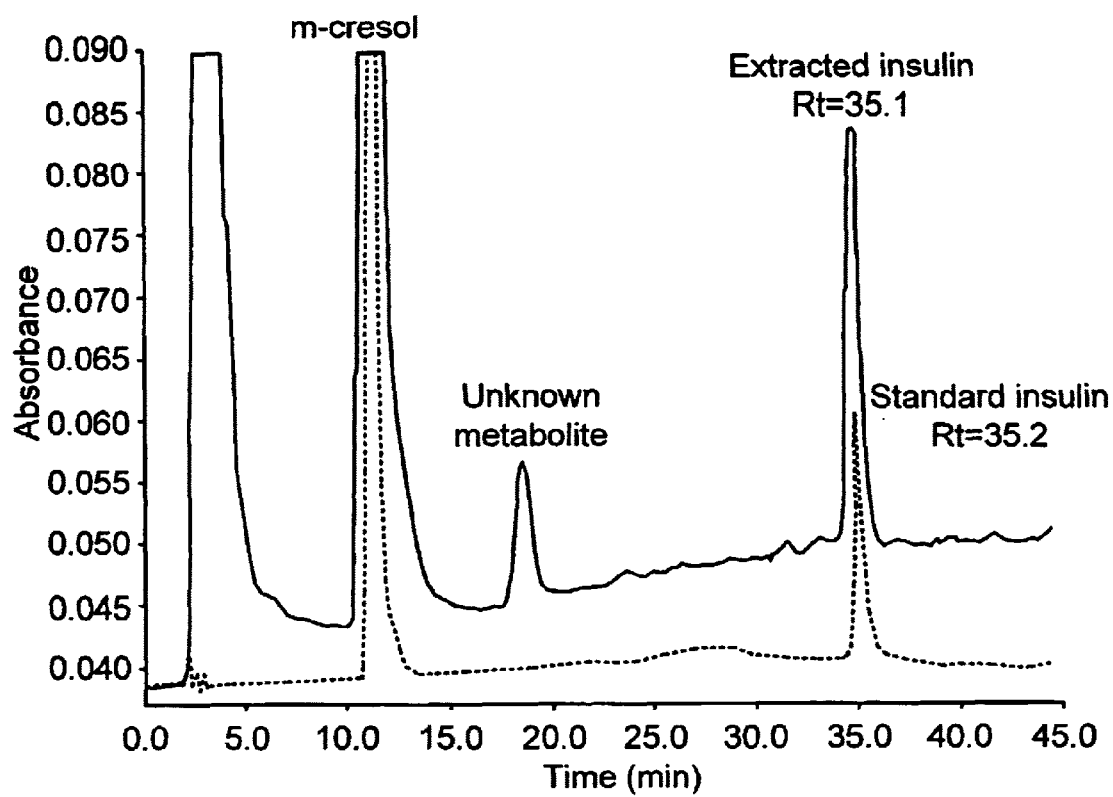

By applying the same HPLC assay used for skin extract that had not been treated with an oxidant (as in FIG. 9A), we injected to the HPLC system on a different day an extract of an iodine-pretreated skin exposed for 2 hours to insulin. FIG. 9B shows that parent insulin was accumulated quantitatively (see 1 unit/ml standard peak for comparison) in the skin, while the delayed peak, which was found in extracts of untreated skin, was not detected. The delayed peak in the non-iodine insulin-treated skin extract (Rt=31.6 in chromatogram FIG. 9A) was identified by HPLC-MS as an insulin dimer form (M. W.=11,884) produced by S—S bonding (FIG. 9C). This is the first mechanistic evidence of insulin skin biotransformation by reduction-oxidation processes.

Comparative Example 13

Figure 10:
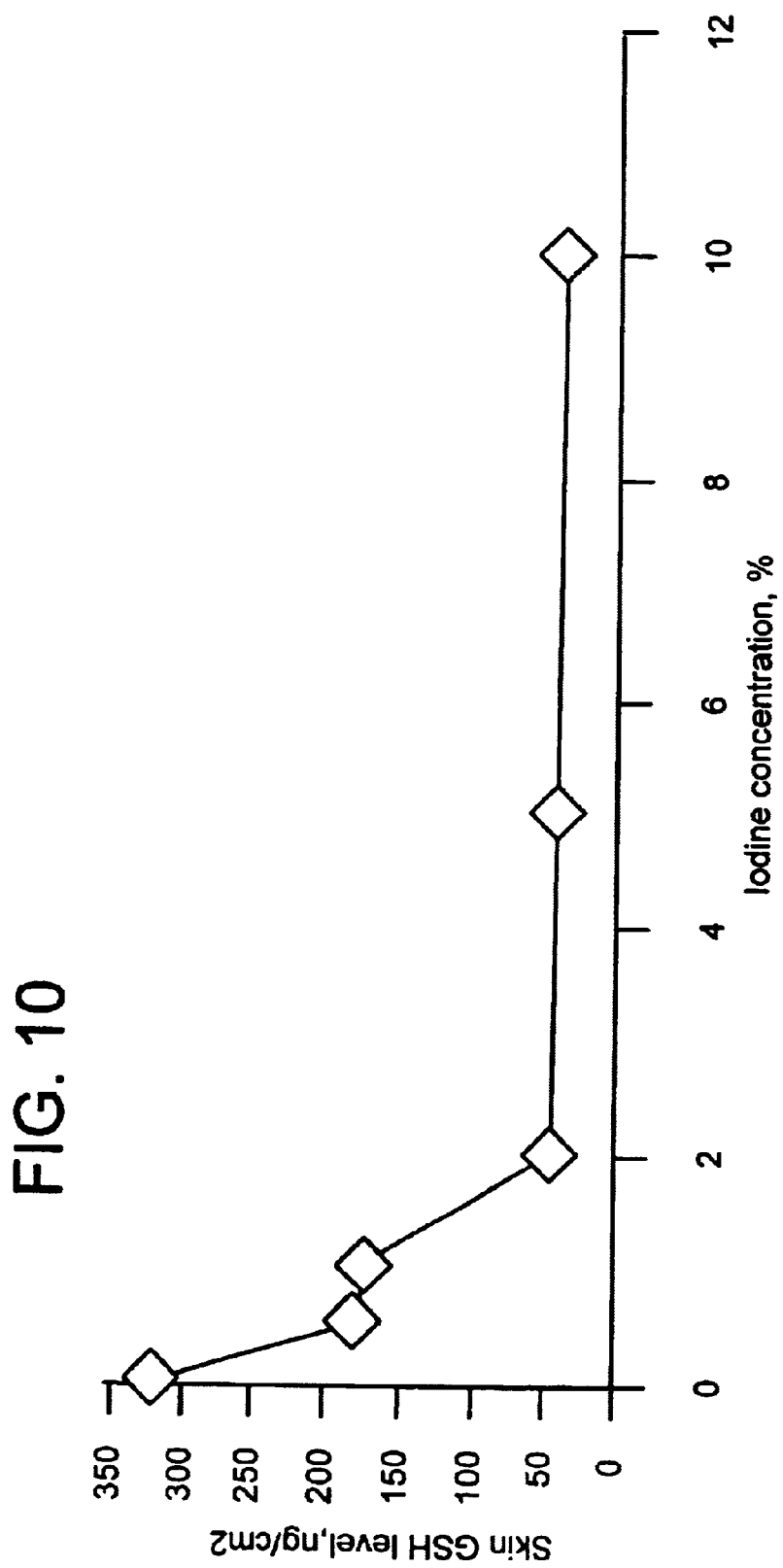

Understanding of the mechanism by which iodine enables percutaneous insulin penetration In a previous example, the molecular mechanism of insulin biotransformation in the skin was evident as well as the role of oxidants to facilitate the transport of the active molecule. In this Example and as a supporting evidence for the previous one, it was shown (see Tables I and II of example 13) that the skin levels of the reducing agents, GSH and γGC, fell off significantly (4.7 fold for GSH and 3.8 fold for γGC) after 2-hour application of 2% iodine solution in tetraglycol-water solution as compared to only vehicle (tetraglycol-water)—treated skin. Although the reduction in these endogenic agents is clear, it has been thought that due to the high GSH level variations, this reduction may not be sufficient to produce a reproducible hypoglycemic effect in all types of skin, especially those containing high levels of reducing agents. It was decided then to test animals for GSH and γGC after application of iodine at various concentrations, ranged from 0.5% to 10%. Preliminary experiments (FIG. 10) demonstrated a correlation between the iodine concentration on the appliaction site and the skin levels of the reducing agents. As shown, the minimum level of GSH obtained after application of about 2% iodine and above. In addition, in a study comparing non-aqueous iodine solutions with those containing water, we have shown (Table III) that the water content in the solution does not make much difference.

TABLE I

GSH levels in skin after application of dermal iodine (2% solution) on anesthetized rats

| Experiment No. | Number of animals | GSH level*, ng/cm² after Vehicle ($GSH_v$) | GSH level*, ng/cm² after Iodine ($GSH_i$) | Ratio, $GSH_v/GSH_i$ |
|---|---|---|---|---|
| 1 | 2 | 2405 (n = 1) | 1205 (n = 1) | 2.0 |
| 2 | 2 | 700 (n = 1) | 110 (n = 1) | 6.4 |
| 3 | 2 | 1480 (n = 1) | 260 (n = 1) | 5.7 |
| 4 | 4 | 2120 ± 297 (n = 2) | 1055 ± 70 (n = 2) | 2.0 |
| 5 | 5 | 1455 ± 1265 (n = 2) | 203 ± 82 (n = 3) | 7.2 |
| Mean $GSH_v/GSH_i$ ratio: | | | | 4.7 ± 2.5 |

*The peptide skin level determined for each animal is an average of analyses of two skin specimens.

TABLE II

γGC levels in skin after dermal iodine (2% solution) was applied on anesthetized rats

| Experiment No. | Number of animals | γGluCys (γGC) level* (ng/cm²) after Vehicle ($γGC_v$) | γGluCys (γGC) level* (ng/cm²) after Iodine ($γGC_i$) | Ratio, $γGC_v/γGC_i$ |
|---|---|---|---|---|
| 1 | 2 | 1100 (n = 1) | 250 (n = 1) | 4.4 |
| 2 | 2 | 860 (n = 1) | 150 (n = 1) | 5.7 |
| 3 | 2 | 150 (n = 1) | 140 (n = 1) | 1.1 |
| 4 | 4 | 870 ± 440 (n = 2) | 140 ± 10 (n = 2) | 6.2 |
| 5 | 5 | 1785 ± 845 (n = 2) | 1190 ± 756 (n = 3) | 1.5 |
| Mean $γGC_v/?\ GC_i$ ratio: | | | | 3.8 ± 2.4 |

*The peptide skin level determined for each animal is an average of analyses of two skin specimens.

TABLE III

GSH skin levels after application of 2% iodine solution - Comparison between aqueous and non-aqueous medium

| Time of dermal application (hours) | Aqueous iodine solution GSH, ng/cm2 | Non-aqueous iodine solution GSH, ng/cm2 |
|---|---|---|
| 2 | 204 | 177 |
| 4 | 188 | 133 |

Comparative Example 14

Experiments with healthy rats

All pharmacodynamic experiments were performed in series of 6 animals each, while making an attempt to withdraw as much information as possible from each series. A typical experimental procedure for each series included application of iodine solution or ointment preparations over the abdominal skin (after hair was trimmed off) for 2–3 hours. The next step was application of Humulin R or other insulin preparations in an open cylinder attached to the skin, covering approx. 1.7 cm² skin surface area.

Figure 11:
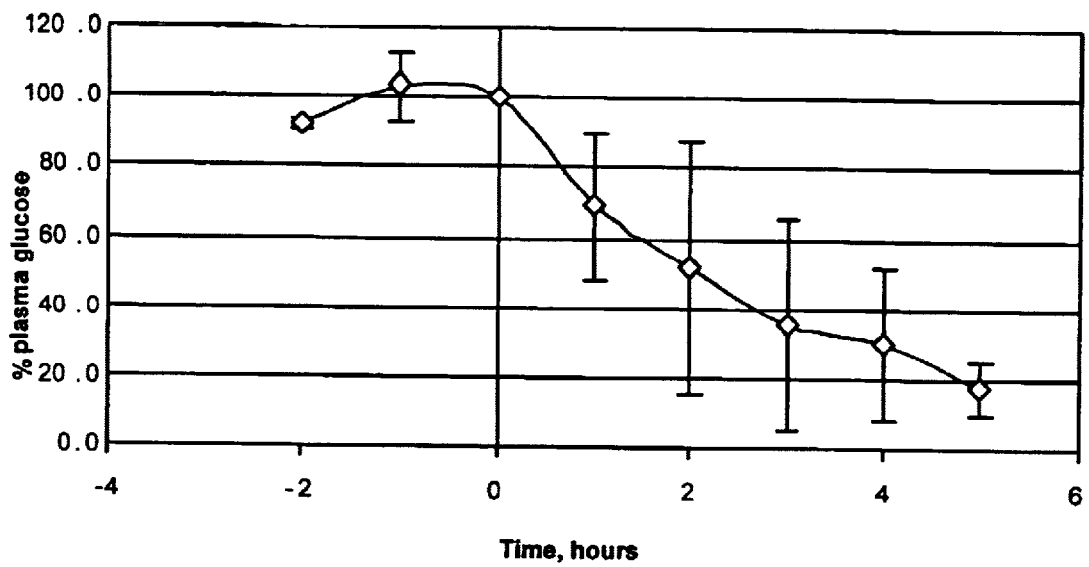

FIG. 11 presents an effect of insulin after its application on iodine-treated skin. This series is similar to the previous series described in examples 5–11, except that the Sprague-Dawley rats weighed 60 grams rather than the usual 300–400 g rats.

Figure 12:
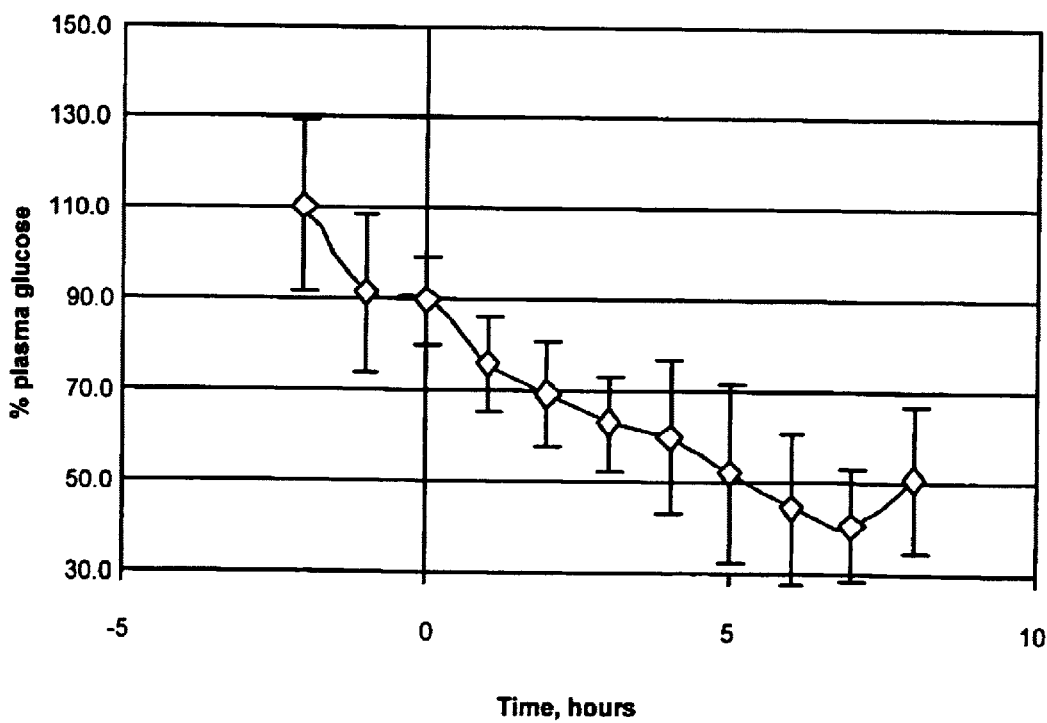
Figure 13:
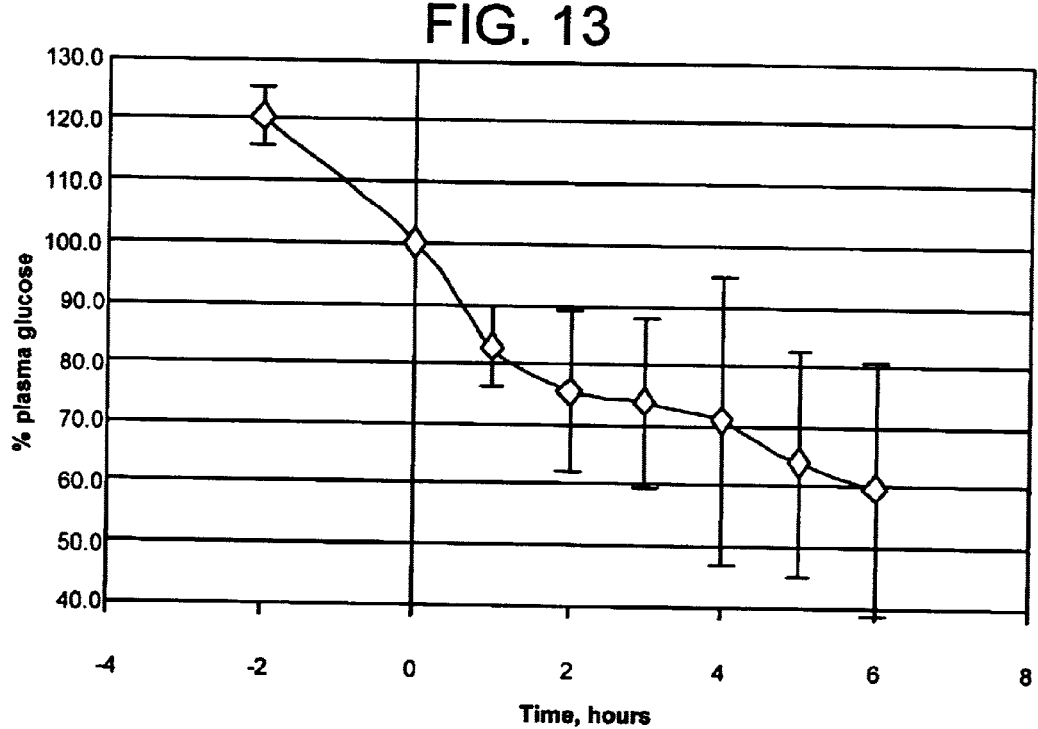
Figure 14:
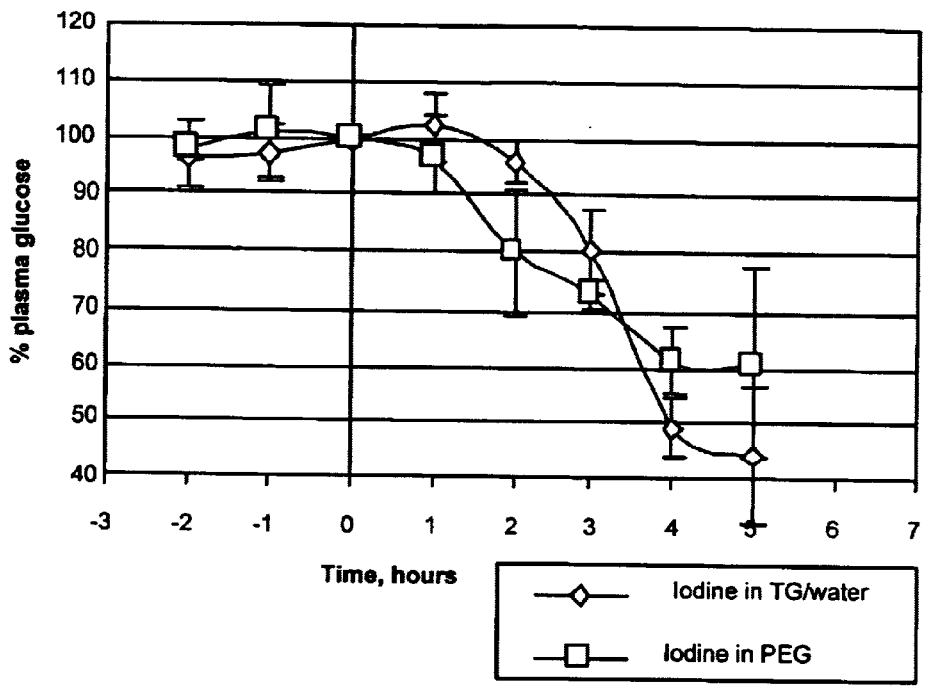
Figure 15:
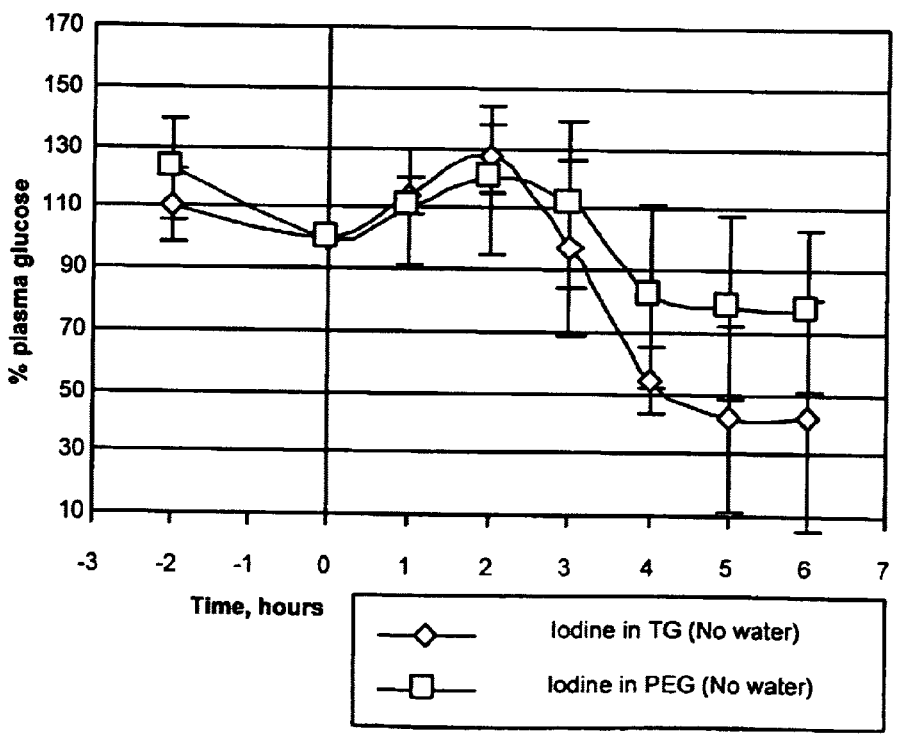
Figure 16:
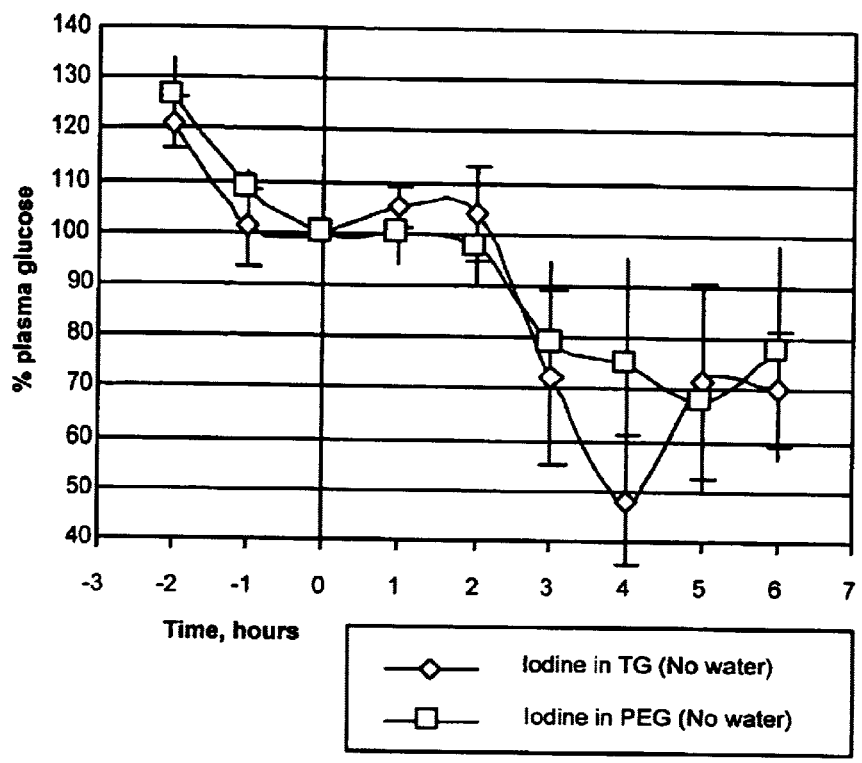
Figure 17:
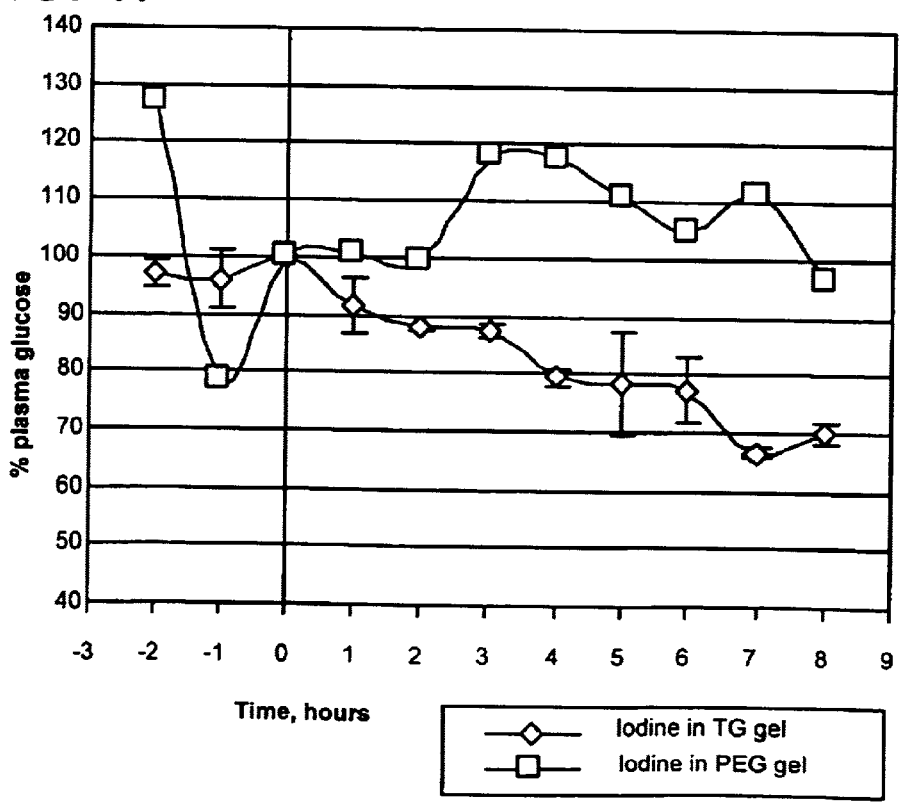

FIGS. 12–17 describe series of experiments performed with Fisher rats. As shown in FIG. 12, this strain of rats positively responded to the procedure like Sprague-Dawley rats. FIG. 13 demonstrates similar effect in Fisher rats by using iodine-containing ointment (actually prepared as a gel) rather than solution. FIGS. 14–17 present four series of experiments aimed to compare between tetraglycol and PEG 400—containing vehicle for iodine preparations. No significant difference was observed between these ingredients in their accelerating effect on insulin penetration. However, the ointment/gel containing PEG was shown to be less effective than the ointment/gel consisting of tetraglycol (FIG. 17). The gel in these series of experiments was prepared by incorporating 10% polyvinylpyrrolidone (see Example 4).

Comparative Example 15

Figure 18:
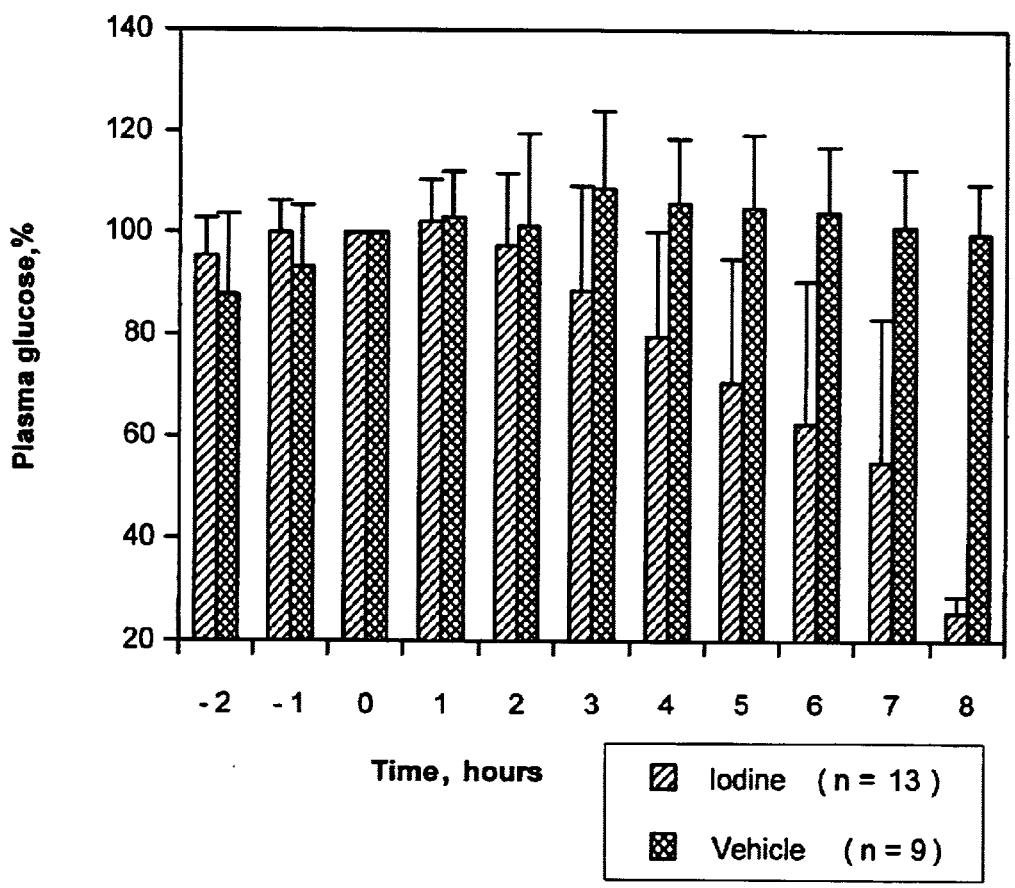

Streptozotocin-induced diabetic rats—evaluation of the iodine effect on plasma glucose upon dermal insulin application A large population of Sprague-Dawley rats (300–500 g) were used for these experiments. The rats were intravenously administered 50 mg/kg streptozotocin (Sigma), and monitored for blood glucose everyday to assure formation of a steady hyperglycemia. The regular procedure was dermal application of 5% topical iodine solution in tetraglycol for 3 hours, and then Humulin R was applied on the open cylinder as usual. Nine control diabetic animals were examined with tetraglycol vehicle pretreatment. FIG. 18 below presents the net effect produced by the iodine pretreatment on 13 diabetic animals.

Comparative Example 16

Figure 19:
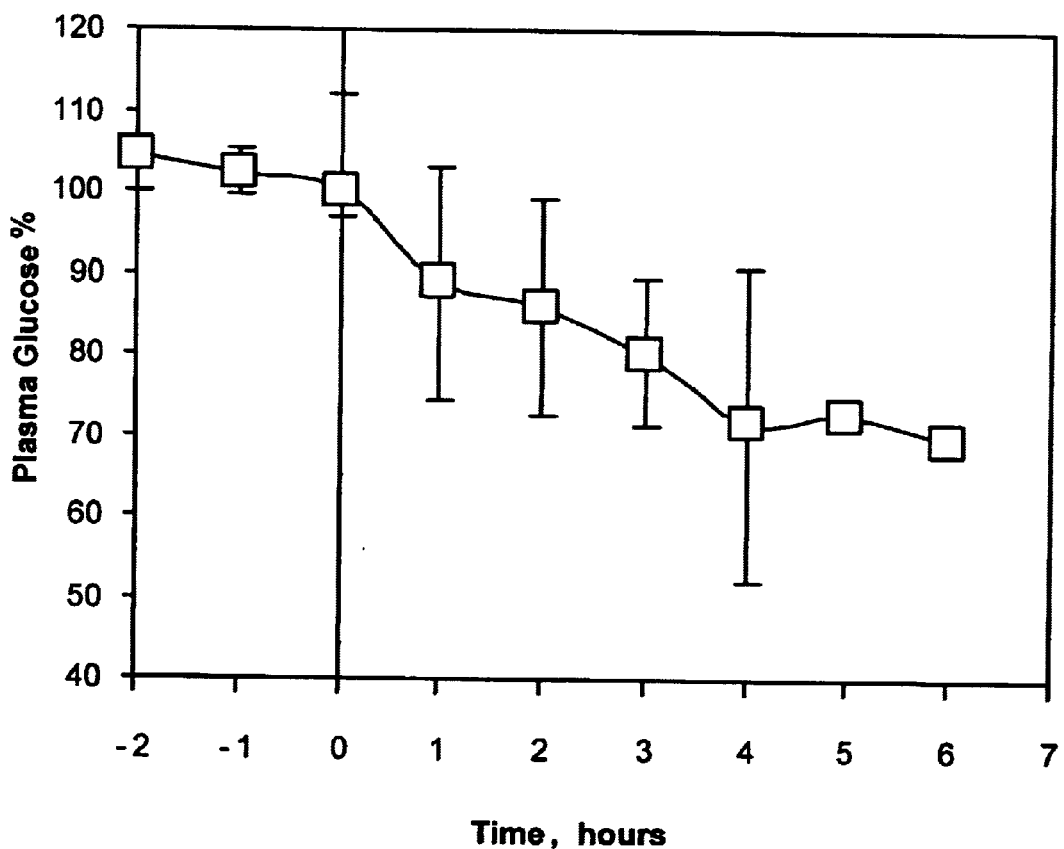
Figure 20:
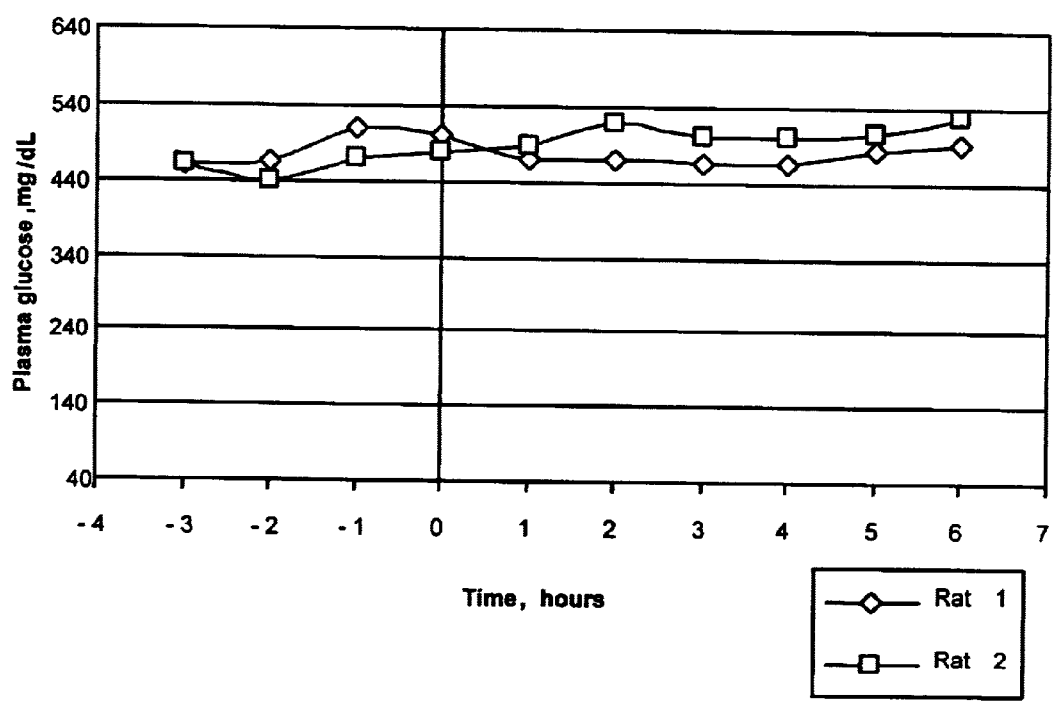

Strentozotocin-induced diabetic pigs—evaluation of the iodine effect on plasma glucose upon dermal insulin application White pigs (10 kgs) were used in similar procedure as in Example 15, except that 150 mg/kg streptozotocin were intravenously injected. The results on 4 pigs are presented in FIG. 19.

Comparative Example 17

Glucose measurements in plasma from diabetic rats applied with dermal insulin composition according to Rothman (WO-A-9000899)

Background for this Example: The compositions described in ROTHMAN (WO-A-9000899) comprise proteins or peptides in the presence of oxidizing and reducing agents. These preparations are used for local treatment of skin pathological disorders (diseased skin) such as acne, eczema, seborrhea and scleroderma. This prior art is not dealing with delivery of proteins through the skin, it is aimed to facilitate skin healing by preparations containing proteins and oxidizers together with reducing agents whose role are not mechanistically clear. In the present invention, however, the oxidizer prevents the reduction of disulfide bond of the exogenous protein via skin penetration, thus, retaining the structure of the active peptide hormone, and enabling its systemic activity. We tested a composition prepared according to Rothman's procedure:

Iodine (0.2 g) was dissolved in 2.5 g tetraglycol. In aseparate vessel, 0.75 g thioglycolic acid were added into 1.55 ml insulin solution (Humulin R, 100 units/ml). The pH was adjusted to 7.6 (as recommended by Rothman) with 3.1 ml 1N NaOH solution. Iodine solution was then mixed with the insulin/thioglycolate solution.

For comparison, we use insulin solution (Humulin R 30–40 units application) after 2–5% iodine in tetraglycol, without reducing agent. Our goal as explained in the application test is neutralize the reducing agent in the skin in-situ, thus protecting insulin from inactivation reactions while transporting from the skin into the blood circulation.

Anesthetized (15 mg/kg pentobarbital sodium i.p.) streptozotocin-induced rats (Sprague-Dawley) after overnight fast, were placed on their back, the abdominal hair was trimmed off, and the skin was washed gently with distilled water. Anesthesia was maintained with 0.1 ml pentobarbital (15 mg/ml) along the experiment. A small cylinder (2.5 cm diameter orifice, 4.9 $cm^2$ surface area) was attached to the central part of the rat abdomen by silicon glue and the insulin preparation (2 ml, 38.2 units) was pipetted into the open cylinder. No change in plasma glucose level (tail vein sampling) was observed 3 hours before application and 6 hours following application (see FIG. 20).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A transdermal delivery system for treating diabetes and other pathologic systemic conditions associated with diabetes, comprising insulin and a pharmaceutically acceptable oxidizing agent selected from the group consisting of iodine, povidone-iodine and sources thereof, said system being essentially free of reducing agents, and wherein said oxidizing agent enables and facilitates the penetration of said active ingredient through the skin layers and into the blood stream.

2. A transdermal delivery system according to claim 1 for treating diabetes and insulin influenced pathologic systemic conditions comprising insulin and a pharmaceutically acceptable oxidizing agent selected from the group consisting of iodine, povidone-iodine and sources thereof, said system being essentially free of reducing agents, and wherein said oxidizing agent enables and facilitates the penetration of said active ingredient through the skin layers and into the blood stream.

3. A transdermal delivery system according to claim 2 wherein said insulin is incorporated into an adhesive patch.

4. A transdermal delivery system according to claim 2 said system further comprising buthionine sulfoximine.

5. A transdermal delivery system according to claim 2 said system further comprising a penetration enhancer.

6. A transdermal delivery system according to claim 5 wherein said penetration enhancer is oleic acid.

7. A transdermal delivery system according to claim 1 wherein said iodine is compounded in tetraglycol.

8. A transdermal delivery system for treating diabetes and other pathologic systemic conditions associated with diabetes, comprising insulin, and a pharmaceutically acceptable oxidizing agent selected from the group consisting of iodine, povidone-iodine, potassium, permanganate, peroxides and silver protein and sources thereof, said system being essentially free of reducing agents, and wherein said oxidizing agent enables and facilitates the penetration of said active ingredient through the skin layers and into the blood stream.

* * * * *